United States Patent
Katsuyama

(10) Patent No.: US 10,874,375 B2
(45) Date of Patent: Dec. 29, 2020

(54) ULTRASOUND DIAGNOSTIC DEVICE AND ULTRASOUND DIAGNOSTIC METHOD

(71) Applicant: FUJIFILM Corporation, Tokyo (JP)

(72) Inventor: Kimito Katsuyama, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 311 days.

(21) Appl. No.: 13/730,231

(22) Filed: Dec. 28, 2012

(65) Prior Publication Data

US 2013/0123628 A1    May 16, 2013

Related U.S. Application Data

(63) Continuation of application No. PCT/JP2011/064890, filed on Jun. 29, 2011.

(30) Foreign Application Priority Data

Jun. 30, 2010  (JP) ................................ 2010-149209

(51) Int. Cl.
   *A61B 8/08*     (2006.01)
   *A61B 6/00*     (2006.01)
   *A61B 8/00*     (2006.01)

(52) U.S. Cl.
   CPC .......... *A61B 8/0858* (2013.01); *A61B 6/469* (2013.01); *A61B 8/485* (2013.01); *A61B 8/463* (2013.01)

(58) Field of Classification Search
   None
   See application file for complete search history.

(56) References Cited

U.S. PATENT DOCUMENTS

| 4,592,237 A * | 6/1986 | Ogura .................... G01N 29/07 73/602 |
| 4,627,290 A | 12/1986 | Ogawa et al. |
| 4,830,015 A | 5/1989 | Okazaki |
| 5,224,480 A | 7/1993 | Yamada et al. |
| 5,465,723 A * | 11/1995 | Angelsen ................. A61B 8/12 600/448 |

(Continued)

FOREIGN PATENT DOCUMENTS

| EP | 0181668 A1 | 5/1986 |
| EP | 2 177 164 A1 | 4/2010 |

(Continued)

OTHER PUBLICATIONS

Wang Zhigang: Study, Application and Development of Ultrasonic Tissue Characterization, Chinese Journal of Medical Imaging, Jan. 20, 1999, vol. 15, Issue 1, pp. 70-72.

(Continued)

*Primary Examiner* — Bill Thomson
*Assistant Examiner* — Shahdeep Mohammed
(74) *Attorney, Agent, or Firm* — Edwards Neils LLC; Jean C. Edwards, Esq.

(57) ABSTRACT

The present invention provides an ultrasound diagnostic device including an ultrasound probe including a plurality of ultrasound transducers transmitting ultrasound waves to an object and receiving ultrasound waves reflected from the specimen to output an ultrasound detection signal, a region-of-interest setting unit setting a region of interest within the specimen, and a variation measuring unit measuring a sonic variation or an attenuation variation of ultrasound waves in the region of interest.

20 Claims, 11 Drawing Sheets

(56) References Cited

U.S. PATENT DOCUMENTS

| | | | |
|---|---|---|---|
| 5,531,117 A * | 7/1996 | Fortes | G01S 7/52049 600/442 |
| 5,810,731 A * | 9/1998 | Sarvazyan | A61B 8/08 600/438 |
| 7,666,138 B2 | 2/2010 | Ogawa | |
| 2005/0015010 A1 * | 1/2005 | Antich | A61B 5/0048 600/449 |
| 2005/0070796 A1 * | 3/2005 | Tsujita | A61B 8/0858 600/437 |
| 2006/0241456 A1 * | 10/2006 | Karasawa | A61B 8/463 600/447 |
| 2008/0275344 A1 | 11/2008 | Glide-Hurst et al. | |
| 2009/0112088 A1 * | 4/2009 | Ohuchi et al. | 600/438 |
| 2010/0040200 A1 * | 2/2010 | Ema et al. | 378/98.12 |
| 2010/0113932 A1 * | 5/2010 | Antich | A61B 5/0048 600/449 |
| 2010/0256493 A1 * | 10/2010 | Chono | 600/443 |
| 2011/0245668 A1 | 10/2011 | Tamura | |
| 2013/0116564 A1 | 5/2013 | Katsuyama | |
| 2013/0131511 A1 * | 5/2013 | Peterson | A61B 5/0048 600/438 |

FOREIGN PATENT DOCUMENTS

| | | |
|---|---|---|
| JP | 60-220051 A | 11/1985 |
| JP | 61-025536 A | 2/1986 |
| JP | 61-087538 A | 5/1986 |
| JP | 03-024868 A | 2/1991 |
| JP | 03-073136 A | 3/1991 |
| JP | 04-035653 A | 2/1992 |
| JP | 05-095946 A | 4/1993 |
| JP | 05-111484 A | 5/1993 |
| JP | 06-070929 A | 3/1994 |
| JP | 06-105841 A | 4/1994 |
| JP | 07-051270 A | 2/1995 |
| JP | 2001-170046 A | 6/2001 |
| JP | 2001-238884 A | 9/2001 |
| JP | 2003-339698 A | 12/2003 |
| JP | 2004-073697 A | 3/2004 |
| JP | 2005-125081 A | 5/2005 |
| JP | 2006-095002 A | 4/2006 |
| JP | 2006-122666 A | 5/2006 |
| JP | 2006-217934 | 8/2006 |
| JP | 2006-255014 A | 9/2006 |
| JP | 2006-296495 A | 11/2006 |
| JP | 2007-007045 A | 1/2007 |
| JP | 2010-051553 A | 3/2010 |
| JP | 2010-099452 A | 5/2010 |
| JP | 2010-193944 A | 9/2010 |
| JP | 2011-224410 A | 11/2011 |
| WO | WO2007/110375 A1 * | 10/2007 |
| WO | WO 2008/139245 A1 | 11/2008 |
| WO | 2009/060751 A1 | 5/2009 |
| WO | WO2009/060751 A1 * | 5/2009 |
| WO | WO 2012/002421 A1 | 1/2012 |

OTHER PUBLICATIONS

Second Office Action issued by State Intellectual Property Office (SIPO) of China dated Dec. 10, 2014 in connection with Chinese Patent Application No. 201180032787.4.

Hachiya H., "Acoustic Characteristics of the Tissue and the Ultrasonic B-mode Image", Medical Imaging Technology, 2003, pp. 95-100, vol. 21 No. 2.

Akamatsu K., "Tissue Characterization by Sound Speed Measurement", Rinshoi (Journal of Clinical Medicine), 1986, pp. 104-108, vol. 12, No. 11.

Maruzen, "Medical Ultrasound Wave—Ultrasound Wave in Living Body", Cho-onpa Binran (Handbook of Ultrasonic Wave), 1999, pp. 420-423.

Non-Final Office Action issued by the USPTO dated Oct. 2, 2015 in connection with U.S. Appl. No. 13/730,379.

Notification of Reasons for Rejection issued by the Japanese Patent Office (JPO) dated Jan. 23, 2015 in connection with Japanese Patent Application No. 2012-522652.

Written Opinion of the ISA issued in International Application No. PCT/JP2013/064496 dated Jul. 30, 2013.

International Search Report issued in International Application No. PCT/JP2013/064496 dated Jul. 30, 2013.

Written Opinion of the ISA issued in International Application No. PCT/JP2013/064495 dated Jul. 30, 2013.

International Search Report issued in International Application No. PCT/JP2013/064495 dated Jul. 30, 2013.

Notification of Reasons for Rejection, issued by Japanese Patent Office dated Feb. 3, 2015 in connection with Japanese Patent Application No. 2012-522653.

2nd Office Action issued by the State Intellectual Property Office of China dated Dec. 16, 2014 in connection with Chinese Patent Application No. 201180032958.3.

International Preliminary Report on Patentability (IPRP), which dated Feb. 21, 2013 in International Application No. PCT/JP2011/064891.

Final Office Action issued by the USPTO dated Jun. 9, 2016 in connection with co-pending U.S. Appl. No. 13/730,379.

Non-Final Office Action issued by the USPTO dated Jul. 11, 2017 in connection with co-pending U.S. Appl. No. 13/730,379.

Advisory Action, issued by the USPTO dated Aug. 20, 2019, in connection with co-pending U.S. Appl. No. 13/730,379.

Non-Final Office Action, issued by the USPTO dated Mar. 6, 2020, in connection with co-pending U.S. Appl. No. 13/730,379.

* cited by examiner

FIG.2
(A)
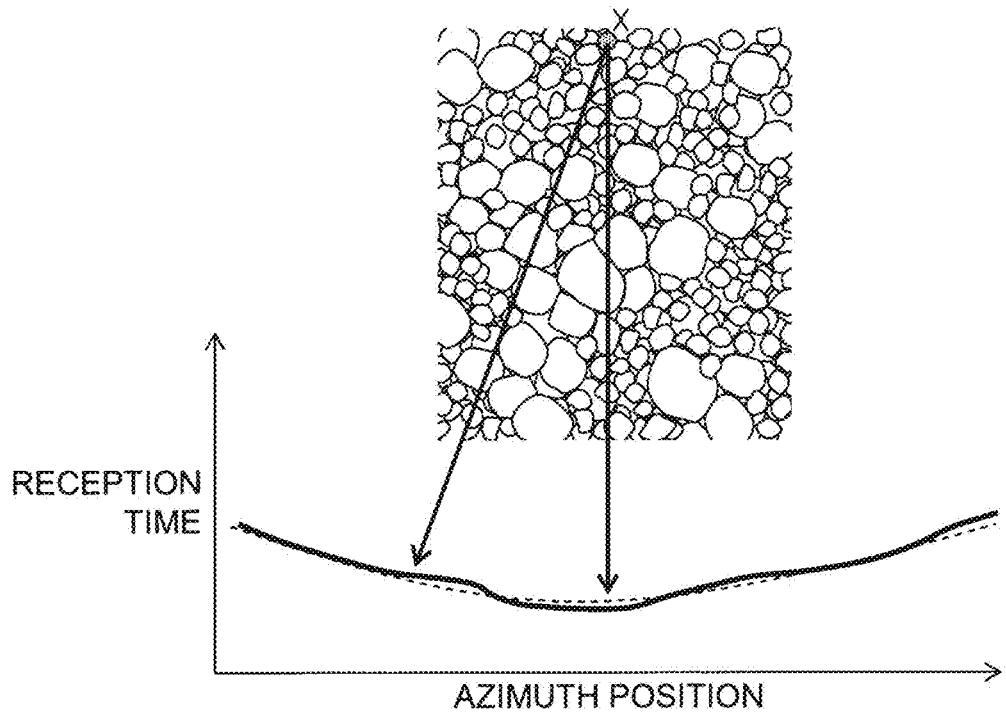
(B)
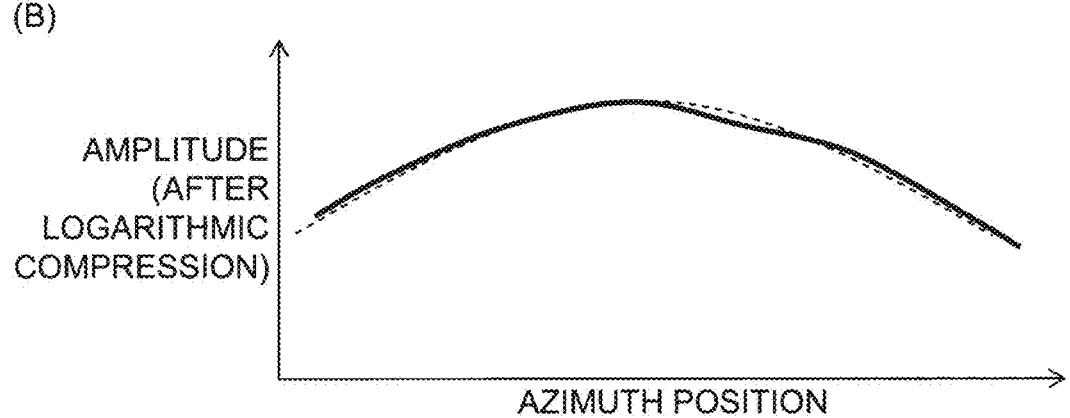
(C)
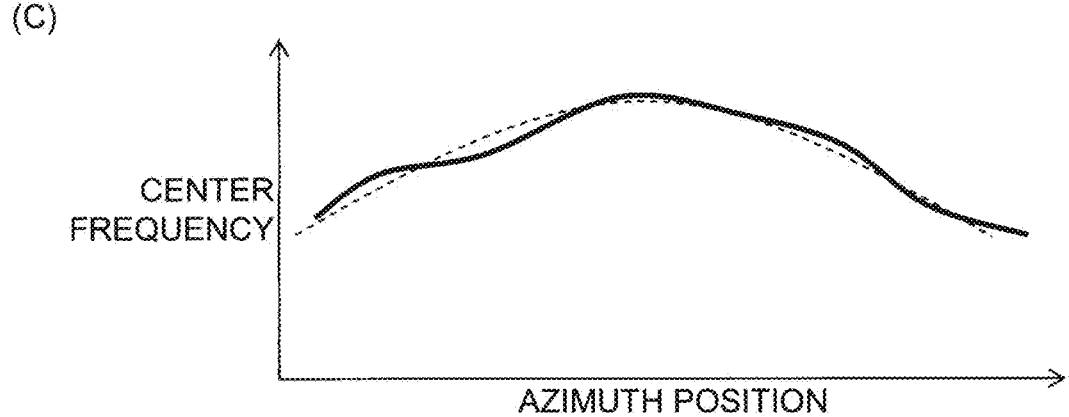

FIG.8
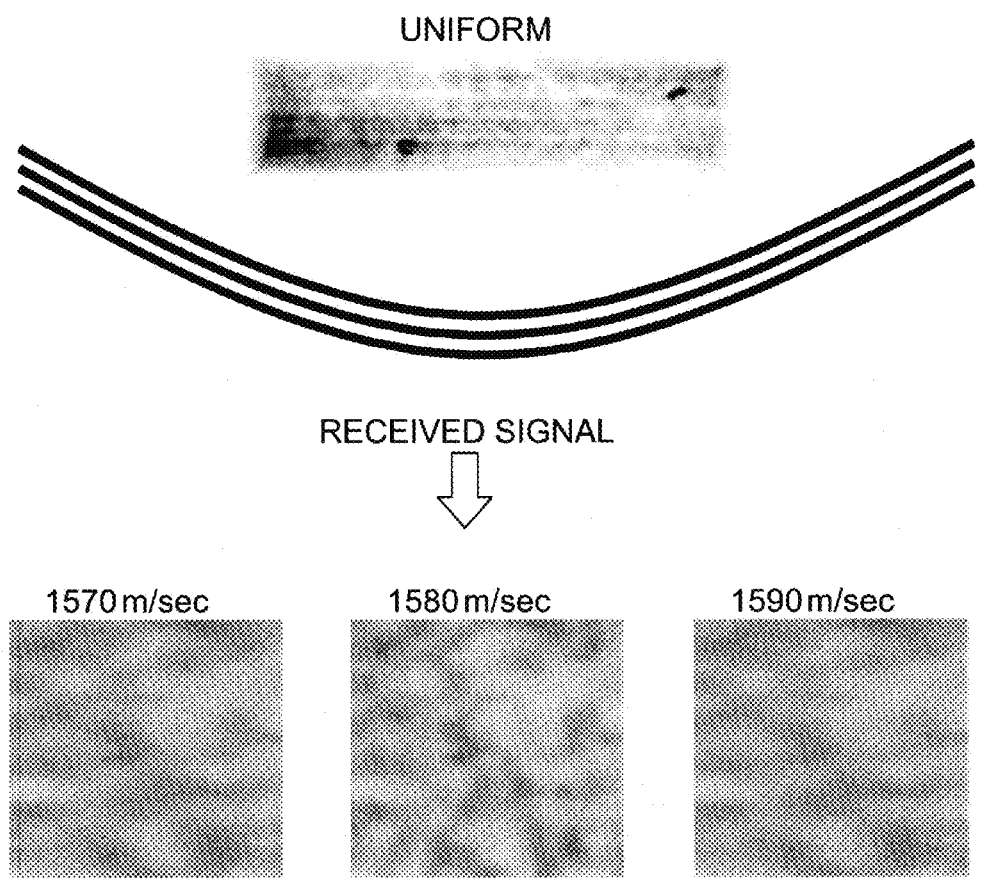
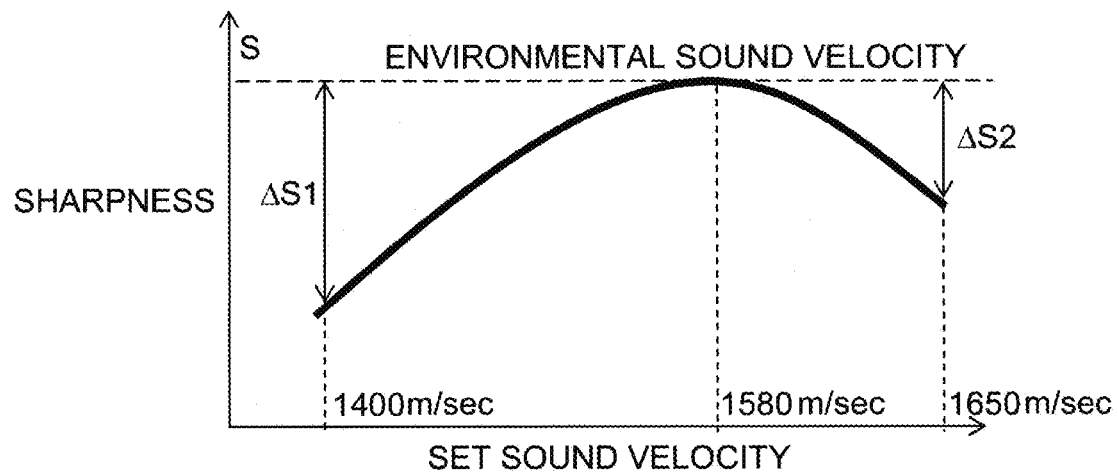

FIG.9
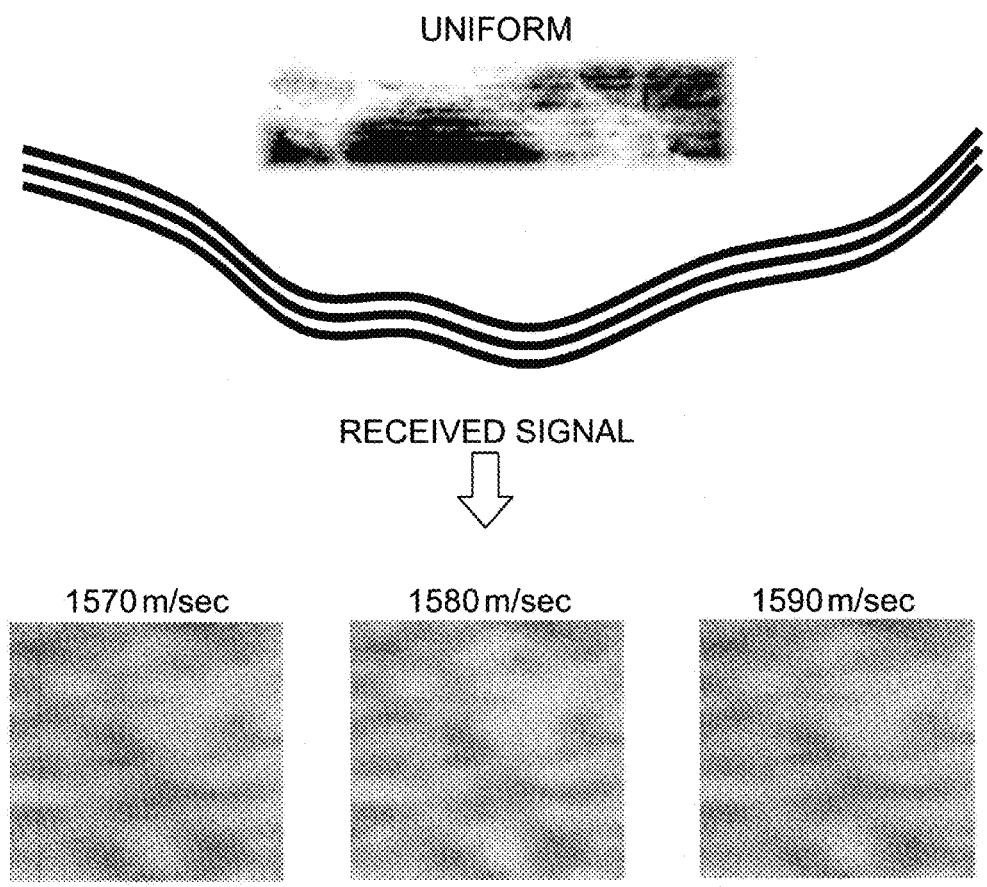
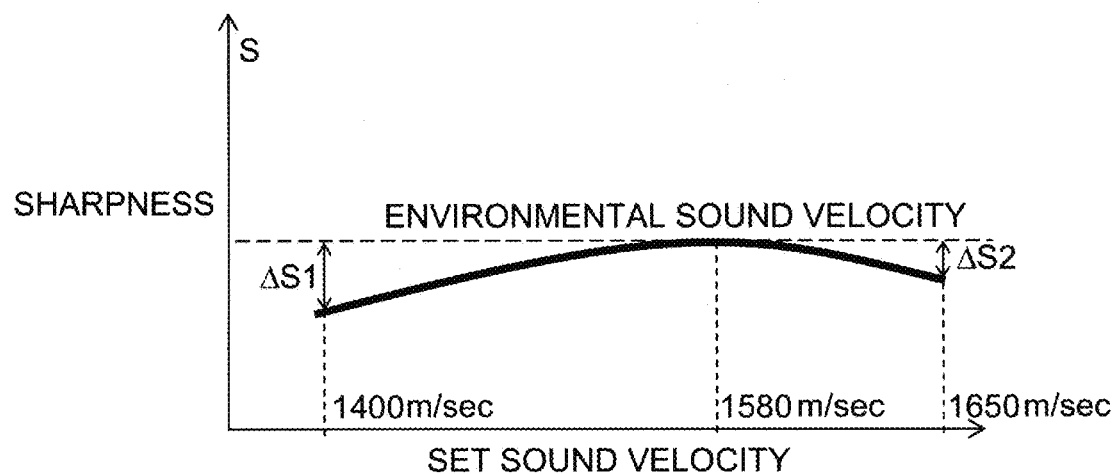

FIG.12
PRIOR ART
(A)
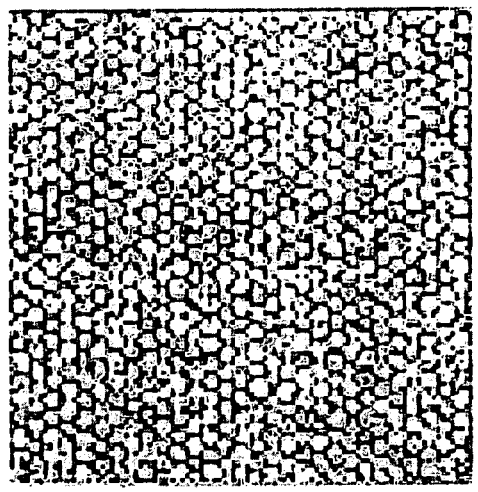
(B)
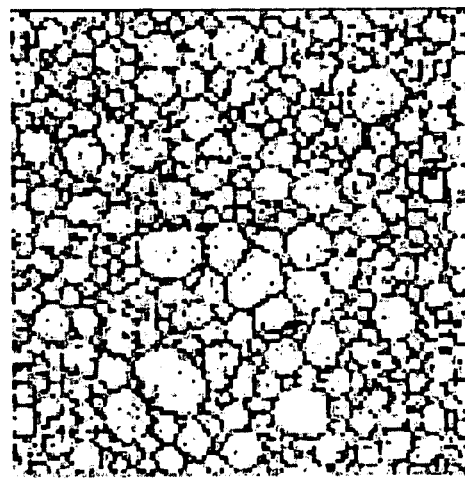
(C)
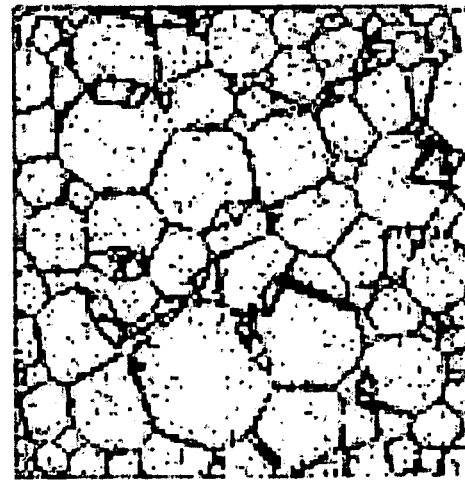

ULTRASOUND DIAGNOSTIC DEVICE AND ULTRASOUND DIAGNOSTIC METHOD

CROSS-REFERENCE TO RELATED APPLICATIONS

This application is a continuation application and claims the priority benefit under 35 U.S.C. § 120 of PCT Application No. PCT/JP2011/064890 filed on Jun. 29, 2011, which was published under PCT Article 21(2) in Japanese, which application designates the U.S., and also claims the priority benefit under 35 U.S.C. § 119 of Japanese Patent Application No. 2010-149209 filed on Jun. 30, 2010, which applications are all hereby incorporated by reference in their entireties.

TECHNICAL FIELD

The present invention relates to ultrasound diagnostic devices and ultrasound diagnostic methods and, in particular, to an ultrasound diagnostic device and ultrasound diagnostic method in which an ultrasound image of a site of an object to be diagnosed is shot and displayed by using ultrasound waves and a tissue characteristic of the specimen is diagnosed based on change of sound velocity or attenuation of the ultrasound waves in a region of interest of the specimen.

BACKGROUND ART

An ultrasound diagnostic device has conventionally been known that shoots and displays an ultrasound image of a site of an object to be diagnosed by using ultrasound waves, and various attempts have been made to measure acoustic characteristics such as sound velocity, attenuation, scattering, or the like of the ultrasound to utilize diagnoses, such as characteristic diagnosis of the inner structure and components of an object's tissue and discrimination of a tissue or a lesion.

For example, Patent Literature 1 discloses a sonic measuring method as described below. Irradiation with an ultrasound wave is made as the angle of irradiation of a transmission transducer is varied and is received as the incident angle of a reception transducer is varied, and an elapsed time between irradiation and reception is measured and stored in memory. On the other hand, based on a virtual sound velocity distribution stored in a sonic memory, the angles of transmission and reception waves of the transmission transducer and the reception transducer are varied on the sonic memory to set respectively corresponding sound line paths. Each required time and the elapsed time previously stored in the memory are compared to find error data. The sound velocity distribution stored in the sonic memory is corrected so that the error data is minimum. With the corrected sound velocity distribution, a sound velocity is found.

Also, Patent Literature 2 discloses a method of extracting and rendering information associated with propagation attenuation inside a living body by taking a spatial difference between band-split detection signals near a depth of interest.

Other than the above, Patent Literatures 3 to 5 and Non-Patent Literatures 1 to 3 can be listed as conventional technologies related to the invention of the present application.

CITATION LIST

Patent Literature

PTL 1: Japanese Patent Application Laid-Open No. 5-95946
PTL 2: Japanese Patent Application Laid-Open No. 7-51270
PTL 3: Japanese Patent Application Laid-Open No. 6-105841
PTL 4: Japanese Patent Application Laid-Open No. 2007-7045
PTL 5: Japanese Patent Publication No. 3-24868

Non-Patent Literature

NPTL 1: Hiroyuki Hachiya, "Acoustic Characteristics of the Tissue and the Ultrasonic B-mode Image" (Medical Imaging Technology, vol. 21, No. 2, March 2003)
NPTL 2: Koichi Akamatsu, "Tissue Characterization by measurement of sound velocity" (Clinical Doctor, vol. 12 no. 11, 1986)
NPTL 3: "Ultrasound Handbook" (Maruzen, 1999)

SUMMARY OF INVENTION

Technical Problem

However, it has been reported that the conventional method of measuring a sound velocity or attenuation described above is macroscopic and, depending on the type of lesion, it is difficult for this macroscopic acoustic characteristic measuring method to grasp microscopic changes in acoustic characteristics.

For example, according to Non-Patent Literature 1: Hiroyuki Hachiya, "Acoustic Characteristics of the Tissue and the Ultrasonic B-mode image" (Medical Imaging Technology, vol. 21, No. 2, March 2003), when the liver suffers from cirrhosis and if liver cirrhosis develops, postnecrotic tissues are coupled together and their surrounding tissues become fibrous to form a node, thereby replacing a hepatic lobule by a reproduced node. For example, FIG. 12 depicts an example of the arrangement of scatterers. (A) portion of FIG. 12 depicts a normal liver, and each hepatic lobule structure has a random size on the order of 1.0 mm to 1.5 mm. In a moderate case of liver cirrhosis as depicted in (B) portion of FIG. 12, a plurality of hepatic lobule structures are destroyed to form fibrous tissues, and each node diameter grows to 3 mm to 4 mm. In a serious case of liver cirrhosis as depicted in (C) portion of FIG. 12 after the lesion develops, the node diameter grows to approximately 7 mm at maximum. It has been reported that a microscopic change in sound velocity structure occurs in a manner such that the sound velocity, attenuation, and scattering inside the nodes are lower than those of the normal liver and, conversely, those of the fibrous portion are higher than those of the normal liver. By contrast, however, according to Non-Patent Document 2: Koichi Akamatsu, "Tissue Characterization by measurement of sound velocity" (Clinical Doctor, vol. 12, no. 11, 1986), it has been reported that there is no significant difference between macroscopic sound velocity values of the normal liver and the cirrhotic liver.

Therefore, the conventionally-suggested macroscopic method of measuring sound velocity or attenuation has a problem in which there is a possibility of being unable to grasp a microscopic change in structure of sound velocity or attenuation as described above.

The present invention was made in view of these circumstances, and has an object of providing an ultrasound diagnostic device and ultrasound diagnostic method capable of grasping a microscopic change in structure of sound velocity or attenuation due to a pathological change, the change being difficult to grasp with conventional measurement of an absolute value of sound velocity or attenuation.

Solution to Problems

To achieve the object above, the invention of the present application provides an ultrasound diagnostic device including an ultrasound probe including a plurality of ultrasound transducers transmitting ultrasound waves to an object and receiving ultrasound waves reflected from the specimen to output an ultrasound detection signal, a region-of-interest setting unit setting a region of interest within the specimen, and a variation measuring unit measuring a sonic variation or an attenuation variation of ultrasound waves in the region of interest.

With this, it is possible to grasp a microscopic change in structure of sound velocity or attenuation due to a pathological change, the change being difficult to grasp with conventional measurement of an absolute value of sound velocity or attenuation.

Also, preferably, the ultrasound diagnostic device includes a point-of-interest setting unit setting at least one or more points of interest within the region of interest, and the variation measuring unit measures the sonic variation based on a change in reception time of a received signal at each of the ultrasound transducers regarding the reflected wave from the point of interest.

Furthermore, preferably, the variation measuring unit measures the attenuation variation based on a change in amplitude or frequency of the received signal at each of the ultrasound transducers regarding the reflected wave from the point of interest.

Still further, preferably, the variation measuring unit measures the attenuation variation based on a change in attenuation at each point of interest within the region of interest.

Still further, preferably, the variation measuring unit measures the sonic variation by comparing RF signals resulting from matching and addition at a constant sound velocity or images for respectively set sound velocities.

Still further, preferably, the ultrasound diagnostic device further includes a transmission focus instructing unit making the ultrasound probe transmit the ultrasound waves by focusing on the region of interest.

Still further, preferably, the transmission focus instructing unit judges an effective region of each transmission focus in advance.

With this, a process of finding a sonic variation or an attenuation variation can be performed at high speed.

Also, similarly, to achieve the object above, the invention of the present application provides an ultrasound diagnostic method, wherein an ultrasound diagnostic device performs a region-of-interest setting step of setting a region of interest within an object, a step of setting at least one or more points of interest within the region of interest, a step of measuring a sonic variation based on a change in reception time of a received signal at each ultrasound transducer regarding a reflected wave from the point of interest, an index calculating step of calculating a variation index from the sonic variation, and a characteristic diagnosing step of diagnosing a tissue characteristic based on the calculated variation index.

With this, it is possible to grasp a microscopic change in structure of sound velocity or attenuation due to a pathological change, the change being difficult to grasp with conventional measurement of an absolute value of sound velocity or attenuation.

Furthermore, similarly, to achieve the object above, the invention of the present application provides an ultrasound diagnostic method, wherein an ultrasound diagnostic device performs a region-of-interest setting step of setting a region of interest within an object, a step of setting at least one or more points of interest within the region of interest, a step of measuring the attenuation variation based on a change in amplitude or frequency of a received signal at each ultrasound transducer regarding a reflected wave from the point of interest, an index calculating step of calculating a variation index from the attenuation variation, and a characteristic diagnosing step of diagnosing a tissue characteristic based on the calculated variation index.

With this, it is possible to grasp a microscopic change in structure of sound velocity or attenuation due to a pathological change, the change being difficult to grasp with conventional measurement of an absolute value of sound velocity or attenuation.

Still further, preferably, in the ultrasound diagnostic method, a transmission focus instructing step of making the ultrasound transducers transmit the ultrasound waves by focusing on the region of interest is further performed.

Still further, preferably, in the transmission focus instructing step, an effective region of each transmission focus is judged in advance.

With this, a process of finding a sonic variation or an attenuation variation can be performed at high speed.

Advantageous Effects of Invention

As described above, according to the present invention, it is possible to grasp a microscopic change in structure of sound velocity or attenuation due to a pathological change, the change being difficult to grasp with conventional measurement of an absolute value of sound velocity or attenuation, and it is possible to diagnose a tissue characteristic by using a variation index representing a sonic variation or an attenuation variation.

BRIEF DESCRIPTION OF DRAWINGS

FIG. 2 is a diagram schematically describing processes of measuring a sonic variation or an attenuation variation.

FIG. 8 is a diagram for describing an image and its sharpness as a result of matching and addition of received signals when the sound velocity of a target tissue is uniform.

FIG. 9 is a diagram for describing an image and its sharpness as a result of matching and addition of received signals when the sound velocity of a target tissue is non-uniform.

FIG. 12 is a diagram for describing changes in tissue characteristics in liver cirrhosis.

DESCRIPTION OF EMBODIMENTS

The ultrasound diagnostic device and ultrasound diagnostic method according to the present invention are described in detail below with reference to the attached drawings.

Figure 1:
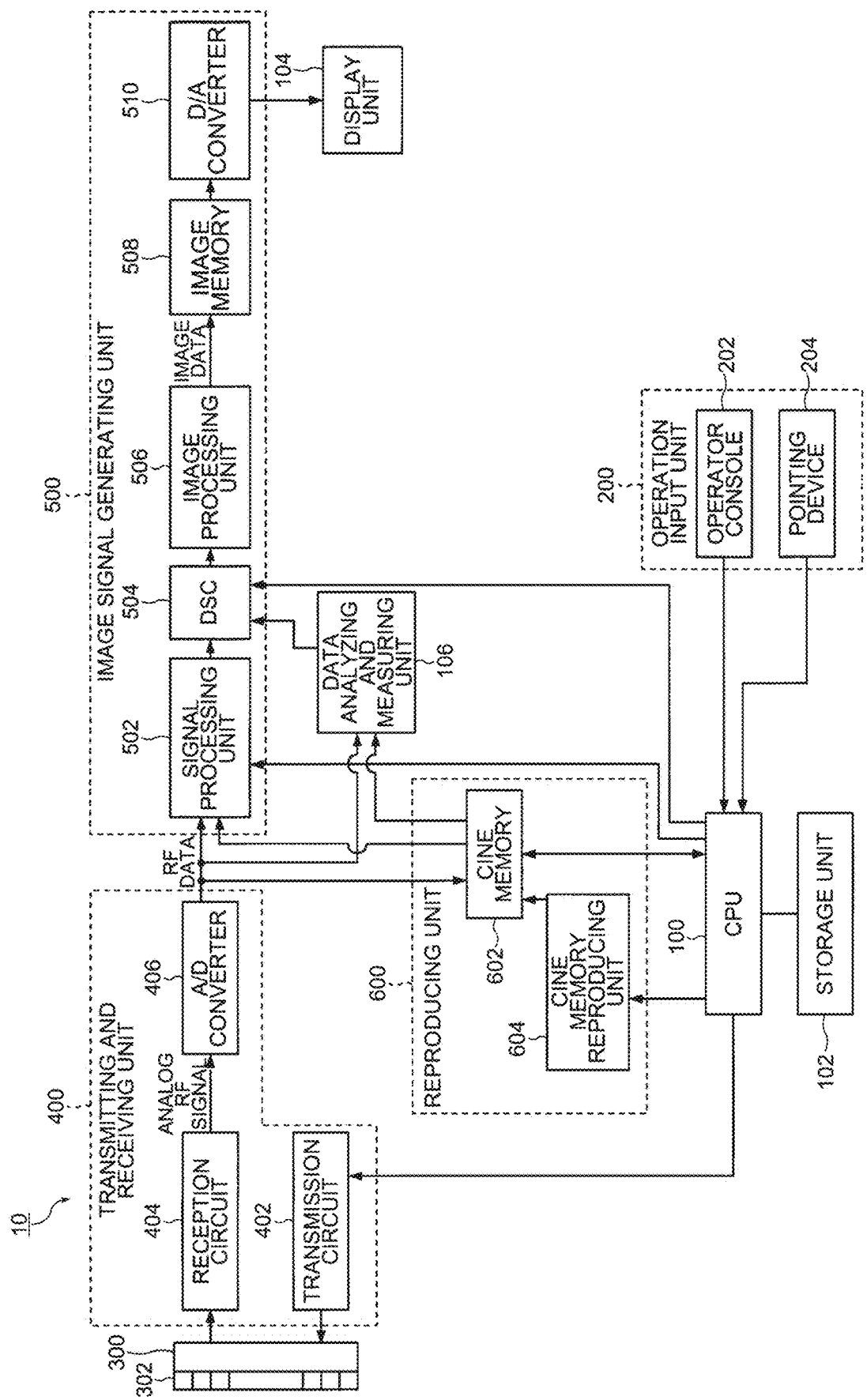
FIG. 1 is a block diagram of a schematic structure of an ultrasound diagnostic device according to an embodiment of the present invention.

FIG. 1 is a block diagram of a schematic structure of an ultrasound diagnostic device according to an embodiment of the present invention.

As depicted in FIG. 1, an ultrasound diagnostic device 10 of the present embodiment is a device in which an ultrasound beam is transmitted from an ultrasound probe 300 to an object OBJ, an ultrasound beam (an ultrasound echo) reflected from the specimen OBJ is received, and an ultrasound image is generated from a detection signal of the ultrasound echo for display.

A CPU (Central Processing Unit) 100 controls each block of the ultrasound diagnostic device 10 according to an operation input from an operation input unit 200.

The operation input unit 200 is an input device accepting an operation input from an operator, and includes an operation console 202 and a pointing device 204. The operation console 202 includes a keyboard accepting an input of character information (for example, patient information), a display mode switching button for switching a display mode between a mode of singly displaying an amplitude image (B-mode image) and a mode of displaying a judgment result of a local sound velocity value, a freeze button for making an instruction for switching between a live mode and a freeze mode, a cine memory reproducing button for making an instruction for cine memory reproduction, and an analysis and measurement button for making an instruction for analysis and measurement of an ultrasonic image. The pointing device 204 is a device accepting an input designated in a region on a screen of a display unit 104, and is, for example, a track ball or a mouse. Note that a touch panel can be used as the pointing device 204.

A storage unit 102 is a memory device having a control program for causing the CPU 100 to control each block of the ultrasound diagnostic device 10, and is, for example, a hard disk or a semiconductor memory.

The display unit 104 is, for example, a CRT (Cathode Ray Tube) display or a liquid-crystal display, displaying an ultrasound image (a moving picture and a still picture) and various setting screens.

An ultrasonic probe 300 is a probe for use as being brought to abut on the specimen OBJ, and includes a plurality of ultrasound transducers 302 configuring a one-dimensional or two-dimensional transducer array. The ultrasound transducers 302 each transmit an ultrasound beam to the specimen OBJ based on a drive signal applied from a transmission circuit 402, and receive an ultrasound echo reflected from the specimen OBJ to output a detection signal.

The ultrasound transducers 302 each include a transducer configured to have electrodes at both ends of a material having piezoelectricity (a piezoelectric element). As an example of the piezoelectric element configuring this transducer, a piezoelectric ceramic made of PZT (Pb (lead) zirconate titanate) or a high polymer piezoelectric element made of PVDF (polyvinylidene difluoride) or the like can be used. When an electrical signal is transmitted to the electrodes of the transducer described above to apply a voltage, the piezoelectric element expands and contracts and, with this expansion and contraction of the piezoelectric element, an ultrasound wave is generated at each transducer. For example, when a pulse-shaped electrical signal is transmitted to the electrodes of the transducer, a pulse-shaped ultrasound wave is generated. Also, when a continuous-wave electrical signal is transmitted to the electrodes of the transducer, a continuous-wave electrical signal is generated. Then, the ultrasound waves generated at the respective transducers are combined to form an ultrasound beam. Also, when an ultrasound wave is received by each transducer, the piezoelectric element of each transducer expands and contracts to generate an electrical signal. The electrical signal generated at each transducer is outputted as a detection signal of the ultrasound wave to a reception circuit 404.

Note that elements of a plurality of types with different ultrasonic conversion schemes can also be used as the ultrasonic transducers 302. For example, a transducer configured of the piezoelectric element described above may be used as an element for transmitting an ultrasound wave, and an ultrasound transducer of an optical detection scheme may be used as an element for receiving an ultrasound wave. Here, the ultrasound transducer of the optical detection scheme converts an ultrasound signal to an optical signal, and may be, for example, a Fabry-Perot resonator or a fiber Bragg grating.

Next, an ultrasound diagnostic process in a live mode is described. The live mode is a mode for displaying and analyzing and measuring an ultrasonic image (moving picture) obtained by bringing the ultrasound probe 300 to abut on the specimen OBJ for transmission and reception of an ultrasound wave.

When the ultrasound probe 300 is brought to abut on the specimen OBJ and an ultrasound diagnosis starts upon an input of an instruction from the operation input unit 200, the CPU 100 outputs a control signal to the transmitting and receiving unit 400 to start transmission of an ultrasound beam to the specimen OBJ and reception of an ultrasound echo from the specimen OBJ. The CPU 100 sets a transmitting direction of the ultrasound beam and a receiving direction of the ultrasound echo for each ultrasound transducer 302.

Furthermore, the CPU 100 selects a transmission delay pattern according to the transmitting direction of the ultrasound beam and also selects a reception delay pattern according to the receiving direction of the ultrasound echo. Here, the transmission delay pattern is pattern data of delay time to be given to a drive signal in order to form an ultrasound beam in a desired direction from the ultrasound waves transmitted from the plurality of ultrasound transducers 302, and the reception delay pattern is pattern data of delay time of reception of the plurality of ultrasound transducers 302. The transmission delay pattern and reception delay pattern described above are stored in advance in the storage unit 102. The CPU 100 selects the transmission delay pattern and the reception delay pattern from those stored in the storage unit 102 and outputs a control signal to the transmitting and receiving unit 400 according to the selected transmission delay pattern and reception delay pattern to control transmission and reception of ultrasonic waves.

The transmission circuit 402 generates a drive signal according to the control signal from the CPU 100 and applies the drive signal to the ultrasound transducers 302. Here, the transmission circuit 402 delays the drive signal to be applied to each of the ultrasound transducers 302 based on the transmission delay pattern selected by the CPU 100. Here, the transmission circuit 402 performs transmission focus in which the timing of applying a drive signal to each of the ultrasound transducers 302 is adjusted (delayed) so that the ultrasound waves transmitted from the plurality of ultrasound transducers 302 form an ultrasound beam. Note that the timing of applying a driving signal may be adjusted so that the ultrasound waves transmitted at one time from the plurality of ultrasound transducers 302 arrive at an entire imaging region of the specimen OBJ.

The reception circuit 404 receives and amplifies an ultrasound detection signal outputted from each of the ultrasound transducers 302. As described above, since a distance between each of the ultrasound transducers 302 and an ultrasound reflection source inside the specimen OBJ is varied, the time when a reflected wave arrives at each of the ultrasound transducers 302 is varied. The reception circuit 404 includes a delay circuit that delays each detection signal by a difference (a delay time) in arrival time of the reflected wave according to the reception delay pattern set based on a sound velocity selected by the CPU 100 (hereinafter referred to as a virtual sound velocity) or a sound velocity distribution. Next, the reception circuit 404 performs matching and addition of the detection signals provided with the delay time, thereby performing a reception focus process. If another ultrasound reflection source is present at a position different from a ultrasound reflection source XROI, an ultrasound detection signal from that other ultrasound reflection source has a different arrival time. Thus, with addition at an addition circuit of the reception circuit 404 described above, the phase of the ultrasound detection signal from the other ultrasound reflection source is cancelled out. With this, the received signal from the ultrasound reflection source XROI is maximum, thereby achieving a focus. With the reception focus process described above, a sound ray signal with the ultrasound echo in focus (hereinafter referred to as an RF signal) is formed.

An A/D converter 406 converts an analog RE signal outputted from the reception circuit 404 to a digital RF signal (hereinafter referred to as RF data). Here, the RF data contains phase information of a received wave (a carrier wave). The RF data outputted from the A/D converter 406 is inputted to a signal processing unit 502 and a cine memory 602.

The cine memory 602 sequentially stores the RF data inputted from the A/D converter 406. The cine memory 602 also stores information regarding a frame rate (for example, a depth of the ultrasound wave at a reflection point, a density of scanning lines, and a parameter indicating a visual field width) inputted from the CPU 100 in association with the RF data described above.

The signal processing unit 502 performs STC (Sensitivity Time gain Control) to correct attenuation of the RF data described above due to distance according to the depth of the ultrasound wave at the reflecting point, and then performs an envelope detecting process to generate B-mode image data (image data representing the amplitude of the ultrasound echo with brightness (luminance) of dots).

The B-mode image data generated by the signal processing unit 502 is obtained by a scanning scheme different from a normal television signal scanning scheme. For this reason, a DSC (Digital Scan Converter) 504 performs conversion (raster conversion) of the B-mode image data described above to normal image data (f, or example, image data of a television signal scanning scheme (NTSC scheme)). An image processing unit 506 performs various necessary image processes (for example, a gray-scale process) on the image data inputted from the DSC 504

An image memory 508 stores the image data inputted from the image processing unit 506. The D/A converter 510 converts the image data read from the image memory 508 to an analog image signal for output to the display unit 104. With this, an ultrasound image (a moving picture) shot by the ultrasound probe 300 is displayed on the display unit 104.

Note that while the detection signal subjected to the reception focus process at the reception circuit 404 is taken as an RF signal a detection signal not subjected to the reception focus process may be taken as an RF signal. In this case, a plurality of ultrasound detection signals outputted from the plurality of ultrasound transducers 302 are amplified at the reception circuit 404, and the amplified detection signals, that is, the RF signals, are subjected to A/D conversion at the A/D converter 406 to generate RF data. And, the RF data described above is supplied to the signal processing unit 502 and also stored in the cine memory 602. The reception focus process is digitally performed at the signal processing unit 502.

Next, a cine memory reproduction mode is described. The cine memory reproduction mode is a mode of displaying and analyzing and measuring an ultrasound diagnostic image based on the RF data stored in the cine memory 602.

When the cine memory reproducing button of the operation console 202 is pressed, the CPU 100 switches the operation mode of the ultrasound diagnostic device 10 to the cine memory reproduction mode. In the cine memory reproduction mode, the CPU 100 instructs the cine memory reproducing unit 604 to reproduce the RF data specified by an operation input from the operator. Based on the instruction from the CPU 100, the cine memory reproducing unit 604 reads the RF data from the cine memory 602 for transmission to the signal processing unit 502 of an image signal generating unit 500. The RF data transmitted from the cine memory 602 is subjected to a predetermined process (the process similar to that in the live mode) at the signal processing unit 502, the DSC 504 and the image processing unit 506 to be converted to image data, and is then outputted via the image memory 508 and the D/A converter 510 to the display unit 104. With this, an ultrasound image (a moving picture or a still picture) based on the RF data stored in the cine memory 602 is displayed on the display unit 104.

In the live mode or the cine memory reproduction mode, when the freeze button of the operation console 202 is pressed while the ultrasound image (the moving picture) is being displayed, the ultrasound image displayed at the time of pressing the freeze button is displayed as a still picture on the display unit 104. With this, the operator can cause the still picture of a region of interest (ROI) to be displayed for observation.

When the measurement button on the operation control 202 is pressed, analysis and measurement specified by the operation input from the operator is performed. When the measurement button is pressed in each operation mode, a data analyzing and measuring unit 106 obtains the RF data before subjected to the image processing from the A/D converter 406 or the cine memory 602 and, by using the RF data, performs the analysis and measurement specified by the operator (for example, a distortion analysis of a tissue part (a hardness analysis), blood flow measurement, measurement of a motion of a tissue part, or measurement of an IMT (Intima-Media Thickness) value). Also, the data analyzing and measuring unit 106 performs a process of measuring a local sound velocity value or calculating an index indicting a variation in sound velocity or attenuation, details of which will be described further below. The analysis and measurement results from the data analyzing and measuring unit 106 are outputted to the DSC 504 of the image signal generating unit 500. The DSC 504 causes the data analyzing and measuring unit 106 to insert the analysis and measurement results into image data of the ultrasound image for output to the display unit 104. With this, the ultrasound image and the analysis and measurement results are displayed on the display unit 104.

Also, when the display mode switching button is pressed, the display mode is switched among a mode for displaying the B-mode image alone, a mode for displaying the judgment results regarding a sound velocity or attenuation variation as superposed on the B-mode image (for example, a display as being colored or with varied luminance according to the sound velocity or attenuation variation or a display with points equal in sound velocity or attenuation variation connected to each other), and a mode for displaying the B-mode image and an image of the judgment results regarding the sound velocity or attenuation variation arranged in a tiled manner. With this, the operator can observe the judgment results regarding the sound velocity or attenuation variation to discover a lesion, for example.

The operation of the ultrasound diagnostic device 10 of the present embodiment is described below.

The present invention sets a region of interest and measures a sonic variation or an attenuation variation in the region of interest, thereby diagnosing a tissue characteristic. In the present invention, although details will be described further below, pseudo point reflection is formed by performing transmission focus; a time difference from a reception time approximated with a constant sound velocity is found from received data of each element; and from variations in time difference, a sonic variation is measured or, from variations in amplitude or variations in frequency approximated with constant attenuation, an attenuation (scattering, absorption) variation is measured. And, the measured variation is utilized for diagnosis of a tissue characteristic.

FIG. 2 schematically depicts processes of measuring a sonic variation and an attenuation variation.

(A) portion of FIG. 2 depicts that a variation is found from a reception time approximated with a constant sound velocity to measure a sonic variation. Also, (B) portion of FIG. 2 depicts that an attenuation variation is measured from a variation in amplitude approximated with constant attenuation. Furthermore, (C) portion of FIG. 2 depicts that an attenuation variation is measured from a variation in center frequency approximated with constant attenuation.

Here, in any of the cases, pseudo point reflection is formed by performing transmission focus and, from received data of each element, a sonic variation or an attenuation variation is measured.

That is, as depicted in (A) portion of FIG. 2, consider pseudo point reflection from a lattice point X of the region of interest ROI within the specimen OBJ. Here, as depicted in (A) portion of FIG. 2, if liver cirrhosis develops to form nodes, a variation occurs in sound velocity or attenuation depending on a traveling direction of an ultrasound wave.

In (A) portion of FIG. 2, a wavefront (reception time) actually measured at each element is represented by a solid line, a wavefront approximated by assuming that the sound velocity of a medium of the specimen OBJ is constant is represented by a broken line, thereby depicting a variation in reception time due to a sonic variation at each azimuth position.

Also, in (B) portion of FIG. 2, an amplitude after logarithmic compression actually measured at each element is represented by a solid line, an amplitude approximated by assuming that attenuation of the medium of the specimen OBJ is constant is represented by a broken line, thereby depicting a variation in amplitude after logarithmic compression due to an attenuation (absorption and scattering) variation at each azimuth position.

Furthermore, in (C) portion of FIG. 2, a center frequency actually measured at each element is represented by a solid line, a center frequency approximated by assuming that attenuation of the medium of the specimen OBJ is constant is represented by a broken line, thereby depicting a variation in center frequency due to an attenuation (absorption and scattering) variation at each azimuth position.

In this manner, the reception time, amplitude, and center frequency of the received wave of pseudo point reflection formed by performing transmission focus have a variation from the reception time, amplitude, and center frequency obtained by assuming constant sound velocity and constant attenuation. This is because a mixture ratio of media with different sound velocities and attenuations is varied in a path corresponding to each azimuth position. And, it can be easily found from FIG. 2 that as a variance in the mixture ratio based on the path is larger, a variation in reception time, amplitude, and center frequency is larger at each azimuth position and, also, as a spatial frequency of the variance in the mixture ratio based on the path is larger, a spatial frequency of the variation in reception time, amplitude, and center frequency is larger.

Therefore, from the magnitude and spatial frequency of the variation in reception time, amplitude, and center frequency of the reflected wave from the lattice point X from the reception time, amplitude, and center frequency obtained by assuming constant sound velocity and constant attenuation, it is possible to obtain information about the magnitude and spatial frequency of the variation in the mixture ratio of the media with different sound velocities and attenuations in the region of interest.

With this, by judging a variation in sound velocity or attenuation, this can be used for diagnosis of a tissue characteristic. Note that while liver cirrhosis has been taken as an example for description herein, it is clear that the present invention can be applied to any, without being restricted to the case of liver cirrhosis.

A process of finding an index (a variation index) indicating a sonic variation or an attenuation variation is described below.

First, how to find a sonic variation is described.

For simplification, it is assumed that media of two types are present in a path when an ultrasound wave propagates from a sound source to an element. This state is schematically depicted in FIG. 3.

Figure 3:
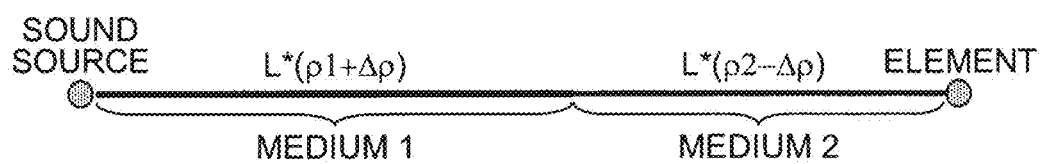
FIG. 3 is a diagram schematically describing the state in which media of two types are present in a path from a sound source to an element.

In practice, unlike the state as depicted in FIG. 3 in which a medium 1 and a medium 2 are present as being clearly separated from each other, they are mixed in a complex manner on their path. FIG. 3 illustrates that the medium 1 and the medium 2 are each gathered to one side so that the mixture ratio can be clearly understood.

In FIG. 3, L represents a total length (a path length) from the sound source to an element, $\rho1$ and $\rho2$ represent average mixture ratios of the medium 1 and the medium 2, respectively, irrespectively of a propagation path, and $\Delta\rho$ represents a change of the mixture ratio described above depending on the path.

Now, it is assumed that the mixture ratio of the medium 1 and the medium 2 is shifted from an average mixture ratio of ρ1:ρ2 by Δρ to become (ρ1+Δρ):(ρ2−Δρ). Of the total length L of the path, a length where the medium 1 is present is L*(ρ1+Δρ) in length and a length where the medium 2 is present is L*(ρ2−Δρ) in length.

When a sound velocity of an ultrasound wave in the medium 1 is taken as v1 and a sound velocity of an ultrasound wave in the medium 2 is taken as v2, a reception time t when the ultrasound wave issued from the sound source of FIG. 3 is received by an element is given by the following equation.

$$t = L*(\rho1 + \Delta\rho)/v1 + L*(\rho2 - \Delta\rho)/v2$$
$$= L*(1/v1)*\rho1 + L*(1/v2)*\rho2 + L*\Delta\rho*((1/v1) - (1/v2))$$

Here, it can be found that if a reception time not depending on the path (not including a path variation)

$$L*(1/v1)*\rho1 + L*(1/v2)*\rho2$$

is subtracted, a change in reception time depending on the path is given by $$L*\Delta\rho*((1/v1) - (1/v2)).$$

When this is divided by the total length (the path length), of the path, the following equation (1) is obtained as an index not depending on the path length.

$$\Delta\rho*((1/v1) - (1/v2)) \qquad (1)$$

However, since the change Δρ of the mixture ratio in the path length L is varied depending on the path, the index represented by Equation (1) above is varied depending on the path.

Thus, if a standard deviation of the values of Equation (1) for all paths, a variation index not depending on the path can be obtained.

Since the change Δρ of the mixture ratio is more largely varied or a difference between v1 and v2 becomes larger due to a pathological change of a tissue, the variation index represented by Equation (1) above is an index satisfactorily representing the degree of variation.

Note that while consideration has been given with media of only two types, if media of two or more types are present, an index (1) for two or more types is a sum of changes Δρ1, Δρ2, . . . of the mixture ratio among different media, and its degree of variation is also an index satisfactorily representing the degree of pathological change.

Note that in the method described above, a reception time, a reception time not including a path variation, and a path length are unknown.

Among these, the reception time (the reception time of the element) can be found by using a known phase aberration analyzing method (for example, refer to PTL 3: Japanese Patent Application Laid-pen No. 6-105841). For received signals of respective elements of the ultrasound probe, a phase difference therebetween is detected by taking a constant signal as a reference signal, and phase difference detection results of adjacent elements are compared with each other and their difference is taken as D. On the other hand, in a graph with each element number of the ultrasound probe being plotted on the horizontal axis and each phase difference between the received signal of each element and a reference signal S being plotted on the vertical axis, 360° is added at discontinuities from positive to negative (that is, when the difference D above is smaller than −180°) and 360° is subtracted at discontinuities from negative to positive (that is, when the difference D above is larger than 180°), thereby changing a discontinuous as curve to a continuous curve. With this, a wide range of phase aberration can be accurately detected.

Also, the reception time not including a path variation can be divided into the path length and $$1/\text{average sound velocity} = ((1/v1)*\rho1 + (1/v2)*\rho2).$$

Next, how to find the path length L and the average sound velocity is described.

Figure 4:
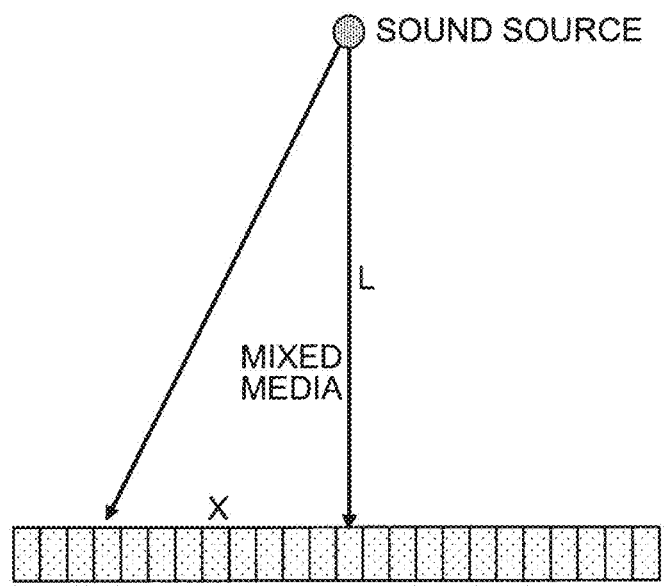
FIG. 4 is a diagram for describing how to find a path length and an average sound velocity in mixed media.

As depicted in FIG. 4, a sound source is assumed at a depth of a distance L from an element surface in a target formed of sonic media (mixed media) of many different types.

First, from each elements received signal of the ultrasound wave issued from the sound source depicted in FIG. 4, a sound velocity (an average sound velocity) and a depth are found by assuming that the medium to the sound source is uniform.

As depicted in FIG. 4, a reception time T(X) at an element at a position with a distance X from straight below the sound source can be given by the following equation.

$$T(x) = \sqrt{(L2+X2)*((1/v1)*\rho1 + (1/v2)*\rho2 + (1/v3)*\rho3 \ldots)} \qquad (2)$$

Here, a sign ρ(A) represents the square root of A, and pn and vn represent a mixture ratio and a sound velocity of a medium n, respectively. Also here, it is assumed that the change Δρ of the mixture ratio is not included.

Since pn can be regarded as constant irrespectively of the propagation path, it can be found that the average sound velocity and the dept with assumption of uniformity is uniquely found from Equation (2) above as in the following Equation (3).

$$1/\text{average sound velocity} = ((1/v1)*\rho1 + (1/v2)*\rho2 + (1/v3)*\rho3 + \ldots)$$

$$\text{depth} = L \qquad (3)$$

The average sound velocity of Equation (3) above is the average sound velocity described above, and each path length can be found from the depth L and the element position X.

That is, by viewing the respective element's reception times in total, the average sound velocity and each path length can be found. Even if the change Δρ of the mixture ratio due to each path is included, this can be considered as less influencing if the respective element signals are viewed in total.

To find the average sound velocity and the depth, a known image analyzing scheme (for example, refer to PTL 4: Japanese Patent Application Laid-Open No. 2007-7045) can be used. This is a method of assuming an average velocity (and a depth) and finding a value with which sharpness and contrast of an image of the sound source are maximum.

Other than the above method, a method may be used in which after each element's reception time is found by phase aberration analysis, least-squares fitting is used to find an average reception time, and its relevant average sound velocity (and depth) is found.

Note that while only propagation from the sound source is assumed herein for simplification, a process in practice is such that pseudo point reflection is formed with transmission focus. In this case, adding only a transmission propagation time to Equation (2) above is enough.

Figure 5:
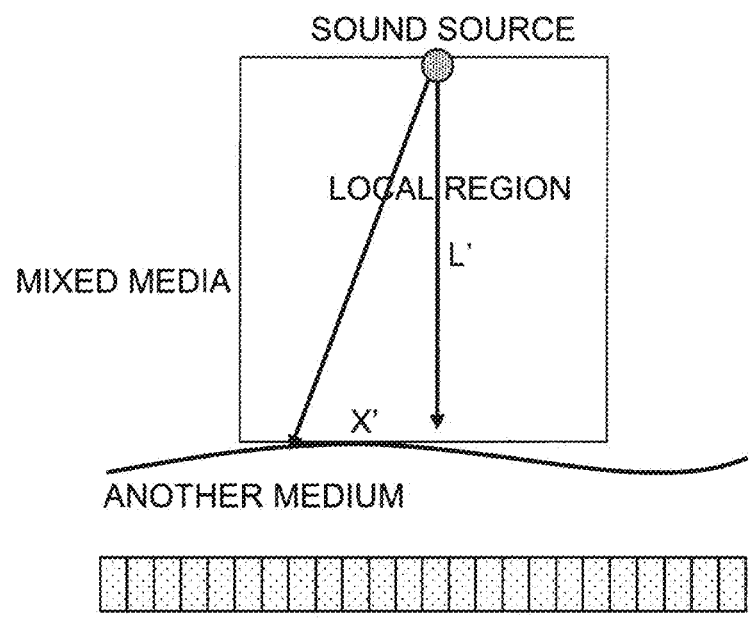
FIG. 5 is a diagram for describing how to find a path length and an average sound velocity when mixed media and another medium are present.

How to find a variation index when a non-uniform layer is present is described below.

here, as depicted in FIG. 5, a variation index is found when another medium different from the mixed media is present in front of each element. Specifically, each path length and a change in reception time are found with an influence of the other medium excluded therefrom.

First, to find each path length, as depicted in FIG. 5, a local region is set so that a portion near a boundary between the mixed media and the other medium forms a lower surface, and a plurality of lattice points are set on this lower surface of the local region. By finding an average sound velocity in this region, a depth L' of the sound source in the local region is found. From this, each path length to each lattice point a distance X' away from there is found.

Here, to find an average sound velocity (a local sound velocity) in the local region, various methods can be used as follows.

For example, with the sound source of FIG. 5 being taken as a point of interest, environmental sound velocities at the point of interest and each lattice on the lower surface of the local region are first found. Here, an environmental sound velocity value is a sound velocity value with maximum contrast and sharpness of an image, and can be found by the image analyzing scheme described above. Next, based on the environmental sound velocity value of the point of interest, a waveform of a virtual received wave WX when the point of interest is taken as a reflection point is calculated. Then an initial value of the assumed sound velocity in the local region is set, the assumed sound velocity is changed by one step, a received wave at each lattice point on the lower surface of the local region is calculated from the environment sound velocity, and a virtually-combined received wave WSUM obtained by virtually combining the received waves with a delay determined by the assumed sound velocity is calculated.

Next, an error between the virtual received wave WX and the virtually-combined received wave WSUM is calculated. The error between the virtual received wave WX and the virtually-combined received wave WSUM is calculated by using, for example, a method of taking a cross-correlation, a method of phase matching and adding by multiplying the virtual received wave WX by a delay obtained from the virtually-combined received wave WSUM or, conversely, a method of phase matching and addition by multiplying the virtually-combined received wave WSUM by a delay obtained from the virtual received wave WX.

Here, to obtain a delay from the virtual received wave WX, with the point of interest being taken as a reflection point, a time when the ultrasound wave propagating with the environmental sound velocity value at the point of interest arrives at each element is taken as a delay. Also, to obtain a delay from the virtually-combined received wave WSUM, an equiphase line is extracted from a phase difference of the combined received waves between adjacent elements, and the equiphase line may be taken as a delay or a phase difference at maximum (peak) positions of the combined received waves of the respective elements may simply be taken as a delay. Furthermore, a cross-correlation peak position of the combined received waves from the respective elements may be taken as a delay. The error at the time of phase matching and addition is found by using, for example, a method of taking peak-to-peak of a waveform after matching and addition or a method of taking a maximum value of the amplitude after envelope detection.

Next, when operations by using all assumed sound velocity values are completed, a local sound velocity in the local region is judged. That is, an assumed sound velocity value with a minimum error between the virtual received wave WX and the virtually-combined received wave WSUM is judged as a local sound velocity value in the local region.

Also, as a method capable of measuring a local sound velocity even when the sound velocity of the specimen is non-uniform and the reception time (received wave) of each cannot be sufficiently approximated with the environmental sound velocity, the following method can be used.

For example, there is a method of finding, in advance, the point of interest in the region of interest and a reception time (a received wave) at each lattice point on the lower surface of the local region and superposing the respective lattice received waves determined by the assumed sound velocity in the region of interest for combination to form a combined received wave, with which the received wave in the region of interest is compared, thereby judging a local sound velocity.

Alternatively, after the point of interest in the region of interest and a reception time (a received wave) at each lattice point on the lower surface of the local region are found in advance, a minimum sum of the propagation time of the ultrasound wave from the point of interest to each lattice point determined by the assumed sound velocity in the region of interest and each lattice reception time for an element is taken as a combined reception time for that element, and the reception time of the received wave at the point of interest and the combined reception time may be compared with each other to judge a local sound velocity.

Note that the point of interest and the reception time at each lattice point on the lower surface of the local region can be found by using the image analyzing scheme and the phase aberration analyzing scheme described above.

Also, another method to find a local sound velocity may be used as follows. For example, similarly to the above, after the reception time (received wave) of each lattice point on the lower surface of the local region is found by the image analyzing and phase aberration analyzing schemes, the lattice received waves are superposed with a delay determined by an assumed sound velocity in the region of interest for combination to form a combined received wave. Based on a delay generated therefrom, an image is generated. That image is analyzed to judge a local sound velocity from a condition that, for example, sharpness is maximum.

An alternative method may be used as follows. After the reception time (received wave) of each lattice point is found, a minimum sum of the propagation time of the ultrasound wave from the point of interest to each lattice point with an assumed sound velocity in the region of interest and each lattice reception time for an element is taken as a delay for that element. Based on that delay, an image is generated. That image is analyzed to judge a local sound velocity from a condition that, for example, sharpness is maximum.

A still alternative method may be used as follows. Similarly to the above, the reception time (received wave) of each lattice point on the lower surface of the local region is found by the image analyzing and phase aberration analyzing schemes. By taking the found time as a delay, each lattice point on the lower surface of the local region described above is regarded as a virtual element. As a received signal of each virtual element, a signal obtained by matching and addition with each delay. From the reception signal of each virtual element, an image is generated based on an assumed sound velocity of the region of interest. That image is analyzed to judge a local sound velocity from a condition that, for example, sharpness is maximum.

Note that each lattice point and the lower surface of the local region described above are taken on a place that is not particularly restricted to a plane but can be set as any curved surface on an element side (a frontward side) of the point of interest. For example, the place is set on an interface of a tissue or lesion.

Next, a change of each element's reception time is found by finding a change from a reception time determined by an average sound velocity from among average sound velocities received at the respective elements, performing a low-frequency cutting process on that change to remove the change due to another medium, and converting each element position to each lattice position on the lower surface of the local region. Since an ultrasound wave propagation path from the point of interest via each lattice to each element is found from the local sound velocity in the local region and the environment sound velocity at each lattice point or each elements reception time, the conversion from each element position to each lattice position on the lower surface of the local region can be made by propagation along this propagation path from each element position in a reversed direction.

Thus found change is divided by each path length to obtain the index given by Equation (1) described above, and its standard deviation can be taken as a variation index.

Next, how to find an attenuation variation is described.

By using the amplitude or the center frequency in place of the reception time of the received signal, an attenuation variation can be found as follows with a scheme similar to that for sound velocity.

There are three types of attenuation: diffusion attenuation due to spread of a sound wave, absorption attenuation due to absorption of a sound wave into a medium for conversion to heat, and scattering attenuation due to scattering of a living tissue. Among these, absorption and diffusion attenuations can be given by $\exp(-\alpha x)$. Here, $\alpha$ represents an attenuation coefficient, and x represents a propagation distance.

According to NPTL 3: "Ultrasound Handbook" (Maruzen, 1999), it can be assumed in a living tissue that the attenuation coefficient $\alpha$ is approximately proportional to frequency in a frequency range of an MHz band. With this attenuation proportional to frequency, a Gaussian pulse has a center frequency shifted in proportion to the propagation distance. By using this, an attenuation can be found from the shift in center frequency.

Next, a variation index of attenuation is considered in a manner similar to that of sound velocity.

An amplitude A(x) of each path from a sound source after logarithmic compression and a center frequency F(x) are given by the following Equation (4).

$$A(x)=A(0)\cdot L^*(\alpha 1^*\rho 1+\alpha 2^*\rho 2)-L^*\Delta\rho^*(\alpha 1-\alpha 2)$$

$$F(x)=F(0)-L^*(\beta 1^*\rho 1+\beta 2^*\rho 2)-L^*\Delta\rho^*(\beta 1-\beta 2) \quad (4)$$

However, regarding the amplitude, influences such as diffusion, transmission focus, non-linear characteristics, and directivity are ignored. Here, $\alpha$ is an attenuation coefficient including an item depending on frequency, and $\beta$ is a constant determined by $\alpha$ and the band of a pulse wave (a Gaussian pulse is assumed).

In Equation (4) above, an amplitude and a center frequency not including a path variation are given by the following Equation (5), $$A(x)A(0)-L^*(\alpha 1^*\rho 1+\alpha 2^*\rho 2)$$

$$F(x)=F(0)-L^*(\beta 1+\beta 2^*\rho 2) \quad (5)$$

By subtracting Equation, (5) from Equation (4) above and dividing the found change $L^*\Delta\rho^*(\alpha 1-\alpha 2)$ in amplitude or change $L^*\Delta\rho^*(\beta 1-\beta 2)$ in center frequency by a path length L, the following Equation (6) is obtained.

$$\Delta\rho^*(\alpha 1-\alpha 2) \text{ or } \Delta\rho^*(\beta 1-\beta 2) \quad (6)$$

With this, an index not depending on the path length is obtained.

Note herein that the path length L is found from an average sound velocity by, for example, Equation (3) above. Also, the amplitude or the center frequency not depending on the path is required to obtain a change, and is found by performing fitting with respect to the amplitude or frequency of each element's received signal. Furthermore, here, fitting may be performed by assuming an average $\alpha$ or $\beta$ based on the depth of the sound source found in Equation (3).

Still further, if a transmission path is also considered, adding the following equation to Equation (4) is enough.

$$-(\text{transmission path length})^*(\alpha 1^*\rho 1+\alpha 2^*\rho 2)$$

Still further, to find a variation index when an nonuniform layer is present, the change represented in Equation (6) above from the average attenuation of the amplitude or center frequency of each lattice on the lower surface of the local region is found. Each path length can be found also when the average sound velocity in the local region is found.

While the examples of how to find the sonic variation and the attenuation variation have been described, a wide variety of finding methods are present.

Figure 6:
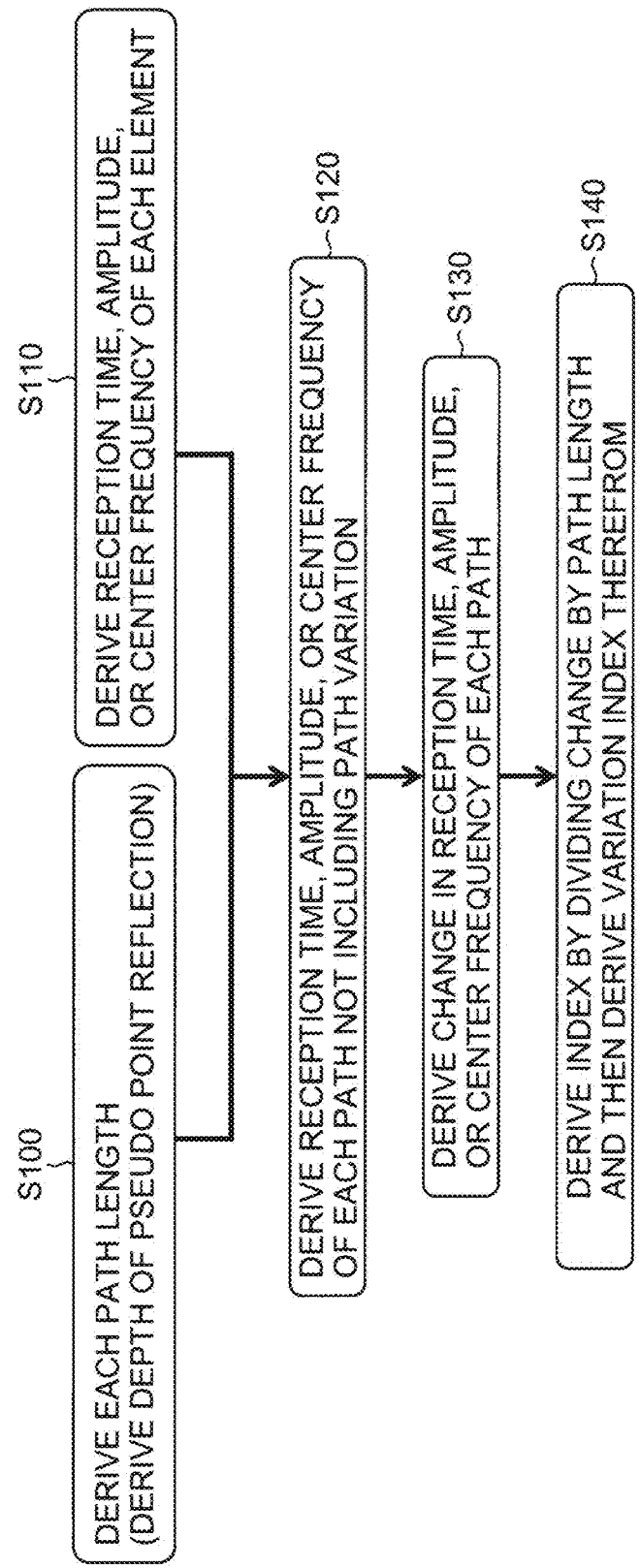
FIG. 6 is a flowchart for describing how to find a sonic variation and an attenuation variation when another medium is not present.
Figure 7:
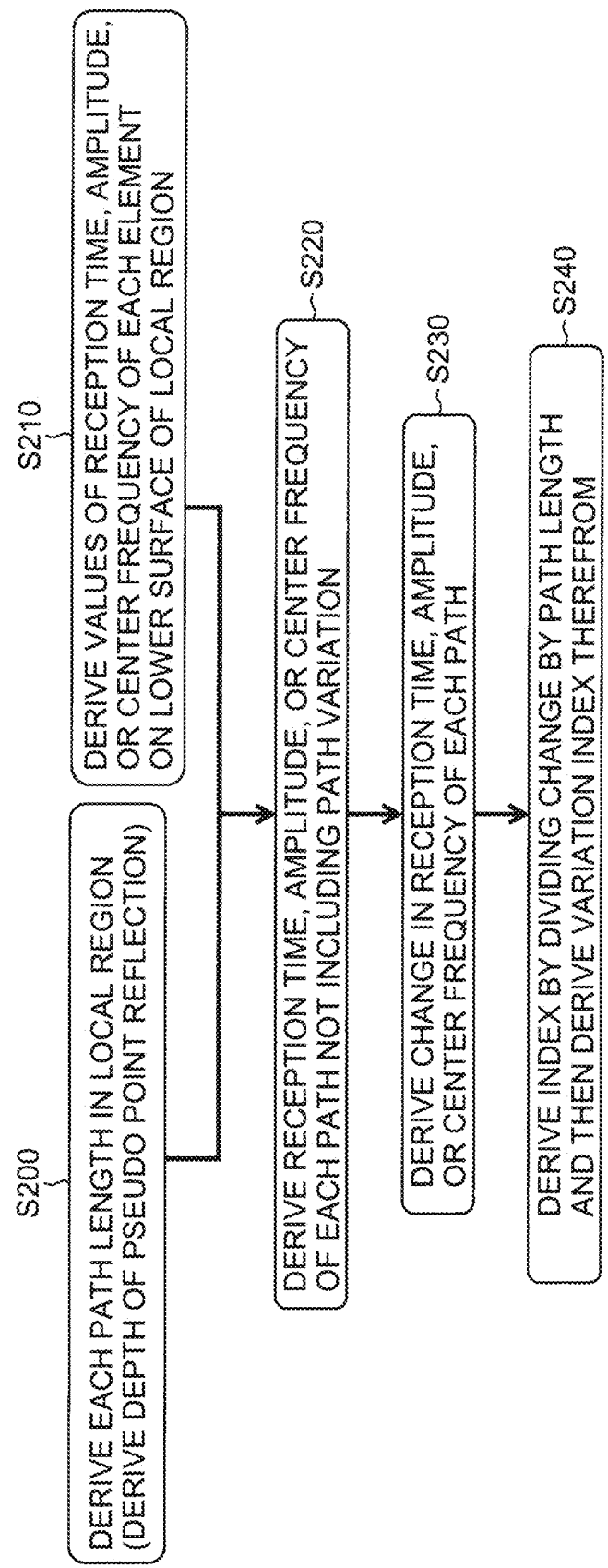
FIG. 7 is a flowchart for describing how to find a sonic variation and an attenuation variation when another medium is present.

FIG. 6 and FIG. 7 collectively depict how to find a sonic variation and an attenuation variation as being divided into steps. FIG. 6 depicts the case without another medium, and FIG. 7 depicts the case with another medium.

Next, processes in a flowchart by the ultrasound diagnostic device 10 in FIG. 6 are described.

First, each path length is derived at step S100 of FIG. 6. If the depth of the point of interest (the sound source) can be derived, each path length connecting the point of interest and each element can be derived.

An example of a method of deriving the depth of the point of interest is as follows.

For example, as a method of finding from reception times, a known image analyzing scheme can be used to find an average sound velocity and depth to the point of interest. Specifically, these can be found so that values of characteristics of sharpness and contrast of an image of the point of interest are maximum.

Alternatively, as a method of finding from amplitudes, a method can be thought in which an amplitude of each element's received signal is obtained, an amplitude found by assuming an average attenuation and depth to the point of interest in Equation (5) above is fitted to each amplitude, and a value with a minimum error is adopted. However, sine the amplitude is influenced not only by attenuation but also by diffusion, transmission focus, non-linear characteristics, and others, it is difficult to apply Equation (5) above. By contrast, by utilizing the method using an amplitude ratio of two frequencies disclosed in PTL 5: Japanese Patent Publication No. 3-24868, the depth can be found from the fact that a difference in amplitude of two frequencies after logarithmic compression is proportional to the attenuation coefficient.

Also, as a method of using center frequencies, a method can be thought in which a center frequency of each element's received signal is obtained, a center frequency found by assuming an average attenuation and depth to the point of interest in Equation (5) above is fitted to each center frequency, and a value with a minimum error is adopted. Here, fitting can be accurately performed if the center frequency at the time of transmission is known.

Also, the reception time, amplitude, or center frequency of each element is derived at step S110 of FIG. 6.

First, as a method of finding a reception time, as described above, a known phase aberration analyzing scheme can be used. Alternatively, phase aberration analysis may be performed by taking a "reception time not including a path variation" found in advance by image analysis of the point of interest together with the average sound velocity as a starting point.

Also, as a method of finding an amplitude, there is a method in which, after envelope detection is performed on each element reception signal for conversion to amplitude information, the value at the reception time described above is obtained. Here, the peak value in a predetermine range may be obtained by taking "the reception time not including a path variation" as a base point.

Also, as a method of finding a center frequency, there is a method of obtaining a predetermined range with the reception time as a base point described above from each element's received signal and finding a barycenter by the following equation after frequency conversion.

$$\int f*P(f)df/\int P(f)df$$

Note in the above equation that f is frequency and P(f) is spectrum density at f.

Furthermore, the center frequency may be a frequency with a peak spectrum density or a center of a half value breadth. Alternatively, the center frequency may be found from the gradient of the phase in a depth direction obtained by performing a detection process.

In the above, the amplitude or the center frequency can be found, with reduced noise and interference, by matching and addition of a signal at a relevant reception time with a predetermined aperture around an element's received signal to be found.

Next, the reception time, amplitude, or center frequency of each path not including a path variation is derived at step S120 of FIG. 6.

First, a reception time can be found if the average sound velocity has been found at step S100 described above. Alternatively, a curve with a minimum error may be fitted to each element's received signal found at step S110. Here, since the path length connecting the point of interest and each element has been found at step S100, a reception time may be calculated by assuming the average sound velocity to find an average sound velocity (reception time) with a minimum error.

Also, an amplitude is found by fitting a curve with a minimum error to the amplitude of each element's received signal found at step S110. Here, since the path length connecting the point of interest and each element has been found at step S100, an amplitude may be calculated by assuming the average attenuation in Equation (5) to find an average attenuation (amplitude) with a minimum error.

To find a center frequency, if the average attenuation has been found at step S100, the center frequency of each element has been found simultaneously. Alternatively, a curve with a minimum error may be fitted to the center frequency of each elements received signal found at step S110. Here, since each path length has been found at step S100, a center frequency may be calculated by assuming the average attenuation to find an average attenuation (center frequency) with a minimum error. Here, if the center frequency at the time of transmission is known, fitting can be accurately performed.

Next, a change in reception time, amplitude, or center frequency of each path is derived at step S30 of FIG. 6. This can be found by subtracting the value found at step S120 from the reception time, amplitude, or center frequency found at step S110.

Next, at step S140 of FIG. 6, an index is found by dividing the change by the path length to derive an index, and then a variation index is derived therefrom. Here, a standard deviation or a maximum value of the index of each path may be taken as a variation index.

Next, by using a flowchart of FIG. 7, how to find a variation index in the region of interest when another medium is present is described.

The flowchart of FIG. 7 is substantially similar to the flowchart of FIG. 6 described above, and is different therefrom in that, in a variation index calculating method for each point of interest, "each path" is replaced by "each path in the local region" and "reception time, amplitude, or center frequency of each element" is replaced by "a value on the lower surface of the local region".

First, each path length in the local region is derived at step S200 of FIG. 7 (a depth of pseudo point reflection is derived). To do this, for example, as depicted in FIG. 5, a local region is set so that each point of interest (sound source) is on an upper surface and a portion near a boundary with the other medium is on a lower surface to find each path length in the local region. To do this, a depth of the point of interest in the local region is first found. As a method for this, a method of finding the dept together with an average sound velocity in the local region is suitably used. Various methods of finding an average sound velocity (a local sound velocity) in the local region are present.

Next, a value of the reception time, amplitude, or center frequency of each element on the lower surface of the local region is derived at step S210 of FIG. 7.

As a method of finding a local reception time of the local region, a reception time (or an average sound velocity) of each lattice on the lower surface of the local region is first found by using know image analyzing and phase aberration analyzing schemes, and is taken as a delay. Also, a reception time (a received wave) of the point of interest is found by image analysis and phase aberration analysis. Then, with each lattice being regarded as a virtual element, as a reception signal of each virtual element, a signal obtained by matching and addition of a received wave of the point of interest with each delay is set. Then, phase aberration analysis is performed on the received signal of each virtual element to find a local reception time of the point of interest. Alternatively, with each lattice being regarded as a virtual element, as a local reception time of each virtual element, the latest time is adopted from among times each obtained by subtracting the delay from each element's reception time of the point of interest.

Alternatively, with received waves of the respective lattices on the lower surface of the local region being regarded as the same, a typical received wave is defined, and by performing deconvolution with the received wave typical among the respective lattices on the lower surface of the local region, a local reception time of the point of interest is found. The deconvolution process can be performed on each element's received signal or on its frequency space.

Alternatively, a search may be made for a local reception time so that an error between the reception time (received wave) of the point of interest and a reception time (received wave) of the point of interest found from the reception time (received wave) of each lattice on the lower surface of the local region and a propagation time (local reception time) from the point of interest to each lattice is minimum. There are various minimum value search algorithms. For example, a quasi-Newton method may be used.

Next, as a method of finding a center frequency, a local reception time or an average sound velocity of the local region, and a reception time or an average sound velocity of each lattice on the lower surface of the local region are found in advance. Then, a propagation path of the point of interest→each lattice→each element is found. Also, the center frequency at the time of transmission is assumed to be known.

An amount of shift in center frequency of each lattice→each element on the lower surface of the local region is found in the following procedure.

First, a center frequency is found from each element's received signal of each lattice (here, the center frequency can be found, with reduced noise and interference, by matching and addition of a signal at a relevant reception time with a predetermined aperture around an element's received signal to be found). Regarding a lattice, a value represented by the following equation is a shift in center frequency on one way.

(center frequency[received signal of a center element]−center frequency[at the time of transmission])/2

A value obtained by subtracting the above value from (center frequency [received signal of each element]−center frequency[at the time of transmission]) represents an amount of shift in center frequency due to attenuation of a propagation path of a lattice→each element.

Even when the center frequency at the time of transmission is unknown, if uniform attenuation is assumed for all paths of a lattice→each element, an attenuation coefficient can be found and an amount of shift can be found (however, higher accuracy is achieved when the center frequency at the time of transmission is known).

By subtracting the amount of shift in center frequency of each lattice→each element from the each element's center frequency of the point of interest, a center frequency at each lattice is found.

Next, as a method of finding an amplitude, an attenuation of each lattice→each element is found in advance from the amount of shift in center frequency, and a propagation path of each lattice→each element is also found in advance. From the amplitude of each element, the attenuation of each lattice→each element is corrected to find an amplitude of each lattice.

Next, a reception time, amplitude, or center frequency of local region not including a path variation is derived at step S220 of FIG. 7.

As a method of finding a reception time, a reception time is found from the average sound velocity and the path length found at step S200. Alternatively, a reception time may be found by fitting a curve with an minimum error at the reception time of each lattice found at step S210. Here, since the path length connecting the point of interest and each lattice has been found at step S200, a reception time may be calculated by assuming an average sound velocity to find an average sound velocity (reception time) with a minimum error.

As a method of finding an amplitude, an amplitude can be found by fitting a curve with a minimum error to the amplitude of each lattice found at step S210. Here, since the path length connecting the point of interest and each lattice has been found at step S200, an amplitude may be calculated by assuming an average attenuation in Equation (5) to find an average sound velocity (amplitude) with a minimum error.

As a method of finding a center frequency, a center frequency is found by fitting a curve with a minimum error to the center frequency of each lattice found at step S210. Here, since each path length has been found at step S200, a center frequency may be calculated by assuming an average attenuation to find an average sound velocity (center frequency) with a minimum error.

In the following, processes at steps S230 and S240 are similar to the processes at steps S130 and S140 of FIG. 6 without another medium described above, and therefore are not described herein.

Note that the lower surface of the local region set when another medium is present may not necessarily be present near the boundary as depicted in FIG. 5, and may not be a plane but a curved surface. Also, to find a reception time, amplitude, or center frequency of each lattice on the lower surface of the local region, transmission focuses are set not only on the local region but also on the lower surface of the local region.

Furthermore, there is a method of performing a low-frequency cutting process on the reception time, amplitude, or center frequency of the signal received at each element to remove a change due to the other medium and converting each element position to each lattice position along the propagation path of each lattice→each element, thereby finding a change in reception time, amplitude, or center frequency of each lattice.

Still further, correction of the other medium and standardization with the path length are not necessarily required. Note that a ratio of the depth and the aperture of an element is desirably constant.

For standardization, examples of an amount to be standardized include a depth, in addition to a path length. Examples of an amount near the depth include a reception time and an amount of shift in frequency of a center element (or lattice). Standardization with these are not required when a variation is evaluated with the depth of the point of interest (the region of interest) (when another medium is present, the depth with the other medium being excluded) being constant.

Still further, from Equation (3) described above and others, it can be found that the sound velocity and attenuation are amounts depending only on Δρ separated from the depth. Therefore, the sound velocity or attenuation may be taken as an index (in this case, it seems that a ratio of the depth and the aperture is not related).

In the case of sound velocity, a sonic variation can be found based on tan RF signal as a result of matching and addition at constant sound velocity or sharpness of an image (a B-mode image) obtained by performing an envelope detecting process on the RF signal (RF data).

FIG. 8 and FIG. 9 depict an image as a result of matching and addition to the reception signal, and its sharpness.

FIG. 8 depicts the case when the sound velocity of a target tissue is uniform, and FIG. 9 depicts the case when the sound velocity of the target tissue is non-uniform.

In FIG. 8 and FIG. 9, with respect to the maximum value of sharpness, a difference of a sharpness at sound velocities at both ends, for example, 1400 m/sec and 1650 m/sec in examples depicted in these diagrams, is used as a variation index. Also, standardization is performed with the maximum value in consideration with luminance dependency.

That is, variation=$(\Delta s1+\Delta s2)/s$.

Other than the above, a maximum sharpness value may be simply taken as the variation index, or a half-value breadth may be taken.

Also, examples of the variation index include the following. That is, there is a sonic or attenuation range in which an absolute value or a mean-square value of a difference from an approximate curve of each sound velocity or attenuation has a minimum predetermined ratio. Also, there are sonic or attenuation ranges on both sides, adjacently to the measured received time, amplitude, or center frequency. Other than the above, in the case of sound velocity, there are a sonic range in which a focus index of an image obtained by matching and addition has a maximum predetermined ratio and a standard deviation of sound velocities and attenuations found by dividing the aperture into small apertures and using each of these small apertures.

Still further, if a variation in ultrasound propagation time, change in amplitude or shift in center frequency of the transmission path is also included, it can be thought that the average sound velocity and the average attenuation themselves become varied depending on the position of the point of interest. Therefore, a standard deviation of variations in average sound velocity or average attenuation of each point of interest in the region of interest may be taken as a variation index.

Next, a variation index based on the spatial frequency is described.

While the variation index described above is an index based on the magnitude of the variation in reception time, amplitude, or center frequency, a varied spatial frequency is thought to be also changed. Specifically, since the frequency of the change in reception time, amplitude, and center frequency with respect to the azimuth position is thought to be changed, the variation index may be based on this frequency.

The change in reception time, amplitude, or center frequency is obtained by the flowchart of FIG. 6 when another medium is not present and by the flowchart of FIG. 7 when another medium is present.

Here, the magnitude of the change in reception time, amplitude, or center frequency increases in accordance with the depth of the point of interest. If the magnitude of the change with respect to each azimuth position uniformly increases, this increase does not influence the frequency, and therefore no correction is required.

However, the degree of increase of change subtly differs depending on each path, and therefore the change may be standardized with each path length for correction. That is, any of the change obtained by the flowchart of FIG. 6 or FIG. 7 and the change obtained by standardization with the path length may be used as an index.

Here, even if the depth of the point of interest is not constant, it is not required to correct the frequency of the change with respect to the azimuth direction by using the depth or the path length. However, evaluation with a constant aperture is desirable.

The center frequency or band of a frequency distribution of thus obtained index with respect to the azimuth position or a variable based thereon is found as a variation index.

For example, in the case of liver cirrhosis, it can be thought that, by replacing uniform and small hepatic lobules by non-uniform and large nodes, the center frequency is moved to a low frequency side or the band is caused to spread. Therefore, it can be thought that the degree of cirrhosis can be diagnosed based on the variation index.

The center frequency is found by $\int f*P(f)df/\int P(f)df$. Here, f represents frequency, and P(f) represents amplitude of the frequency f. Other than that, as the center frequency, a frequency with a maximum amplitude, a center frequency of a band with an amplitude being at a predetermined maximum ratio, or a frequency with an integral value of P(f) being a half value may be taken.

The band can be found by finding the square root of $\int f(f-f0)2*P(f)df/\int P(f)df = \int f2*P(f)df/\int P(f)df - f02$. Here, f0 represents a center frequency. This may be kept as dispersed. Other than that, as the band, a band with an amplitude of the center frequency or a predetermined ratio of a maximum amplitude or a band in which an integral value of P(f) with the center frequency or the frequency for a maximum amplitude as a center is at a predetermined ratio of all integral values.

Other than the center frequency and the band, a distortion in frequency distribution may be found as a variation index. This can be found from tertiary moment $\int (f-f0)3*P(f)df/\int P(f)df$.

While the method of finding a variation index by taking a change in reception time, amplitude, or center frequency or a change in standardization of the path length as an index has been described above, not the change but the reception time, amplitude, or center frequency may be directly taken as an index. In this case, since a component of "the reception time, amplitude, or center frequency not including a path variation" is included in extremely low frequencies of the frequency distribution. Thus, extremely low frequency components can be removed when the variation index is calculated.

Also, a variation index may be found based on the spatial space of variation in average sound velocity or average attenuation due to the position of the point of interest. In this case, a two-dimensional frequency distribution of an average sound velocity or an average attenuation in the region of interest is found, and a variation index can be found from the center frequency, band, or distortion thereof.

Next, an entire process for finding a variation index representing a sonic variation or an attenuation variation is described.

Figure 10:
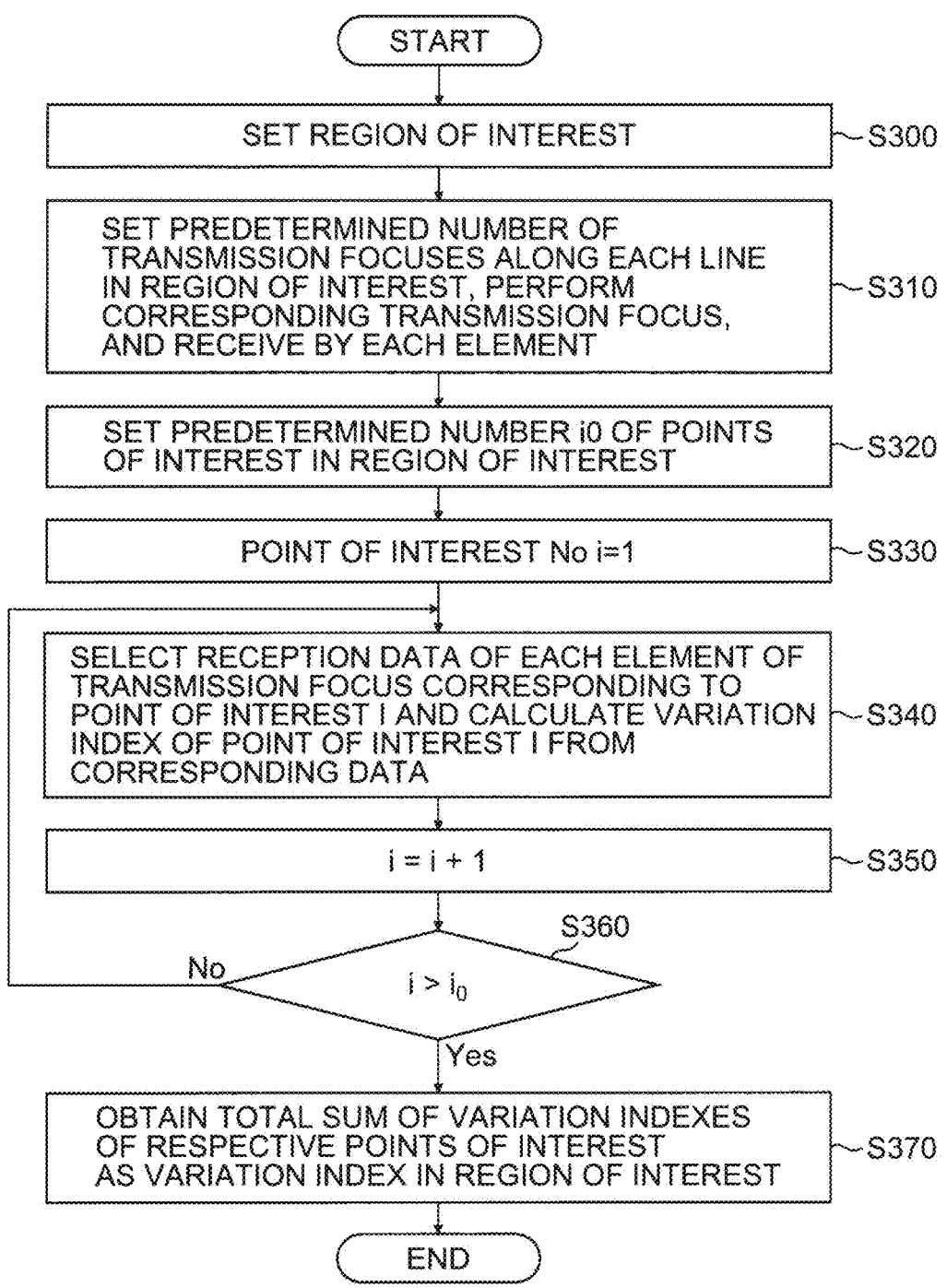
FIG. 10 is a flowchart of an entire process to find a sonic variation or an attenuation variation.

FIG. 10 is a flowchart of an entire process to find a sonic variation or an attenuation variation.

First, a region of interest is set at step S300 of FIG. 10.

Next, at step S310, a predetermined number of transmission focuses are set along each line in the region of interest, relevant transmission focus is performed, and reception is made by each element.

Here, to select a transmission focus corresponding to each point of interest, an effective region of each transmission focus may be judged in advance as follows.

That is, a transmission focus No(n) is first set, a specified line width is added/subtracted to/from a predetermined specified line No to set a line No(m), and each element's received signal of the focus No(n) and the line No(m) is read. Next, a set sound velocity No(k) is set, reception focus with the set sound velocity No(k) is performed on the received signal of the line No(m) of the transmission focus No(n), and an index or image is stored. This process is repeatedly performed with the set sound velocity No being varied. When processes with predetermined set sound velocities are completed, the line No is changed, and transmission focus is performed again on a new line No with the set sound velocity No(k) being varied as described above.

Next, an environmental sound velocity (an average sound velocity) of each depth is found from the indexes or images of all lines with each set sound velocity, a standard deviation of environment sound velocities in a depth direction is calculated, a minimum point is judged as an actual focus depth, and an effective region of the transmission focus No(n) is found. Then, the transmission focus No is changed, and an effective region for the next transmission focus No is found in the same manner as above.

Note that transmission focus is performed correspondingly to each point of interest.

Next, at step S320, a predetermined number (i0) of points of interest are (is) set in the region of interest. The number of points of interest may be one, that is, the predetermined number i0 may be 1.

Then, for each of i0 points of interest, a variation index representing a sonic variation or an attenuation variation at that point of interest is found.

First, at step S330, i indicating a point-of-interest number is set at 1 (i=1).

Then, at step S340, each element's received data of transmission focus corresponding to an i-th point of interest is selected, and a variation index representing a sonic variation or an attenuation variation at the i-th point of interest is found from the relevant data.

To find a variation index, if another medium is not present, a variation index is found by the method depicted in the flowchart of FIG. 6 described above. If another medium is present, a variation index is found by the method depicted in the flowchart of FIG. 7 described above. Here, separately from the region of interest, a local region is set, and each elements received data of transmission focus corresponding to each lattice point on the lower surface of the local region is also used.

Next, at step S350 of FIG. 10, the point-of-interest number i is incremented by 1 (1 is added to i). At the next step S360, it is determined whether i exceeds the number of points of interest (the predetermined number i0).

As a result, if i has not exceed i0 yet, the procedure returns to step S340, repeating the process of finding a variation index representing a sonic variation or an attenuation variation at the i-th point of interest described above.

On the other hand, if it is determined that i exceeds i0, the procedure goes to the next step S370.

At step S370, a total sum of variation indexes of the respective points of interest is obtained, which is taken as a variation index in the region of interest.

In this manner, while a total sum of variation indexes of the respective points of interest is taken herein as a variation index of the region of interest, in place of the total sum, after the indexes of the respective points of interest are all collected, their standard deviation may be taken as a variation index of the region of index.

Alternatively, if another medium is present in front of the region of interest, other than the method depicted in the flowchart of FIG. 7 described above, a variation index at each point of interest in a shallow region and a variation index in a deep region in the region of interest may be compared and analyzed. With this, a variation index with a reduced influence of the other medium can be found in a simplified manner. For example, a total sum of gradients of change of variation indexes of the respective points of interest in a depth direction or a total sum of differential values from the variation indexes at the points of interest in the shallow region or standardized values may be taken for each line and may be taken as a variation index of the region of interest. Alternatively, since the influence of the other material on the variation in the deep region is small, a total sum of variation indexes in the deep region may be taken as a variation index of the region of interest.

In the examples described so far, a variation in time, amplitude, or frequency of received signals occurs in the course of propagation from pseudo point reflection, and that variation is found. However, this variation in time, amplitude, or frequency of received signals occurs not only in the course of propagation from pseudo point reflection but also due to ambient interference at the time of forming pseudo point reflection.

Specifically, when the transmission focus does not concentrate on one point due to unevenness in sound velocity, attenuation, or scattering or when ambient interference is larger than the point of interest due to unevenness in scattering, the received signal undergoes interference of ambient scattering. As a result, variations in time, amplitude, and frequency of the received signal occurs.

Figure 11:
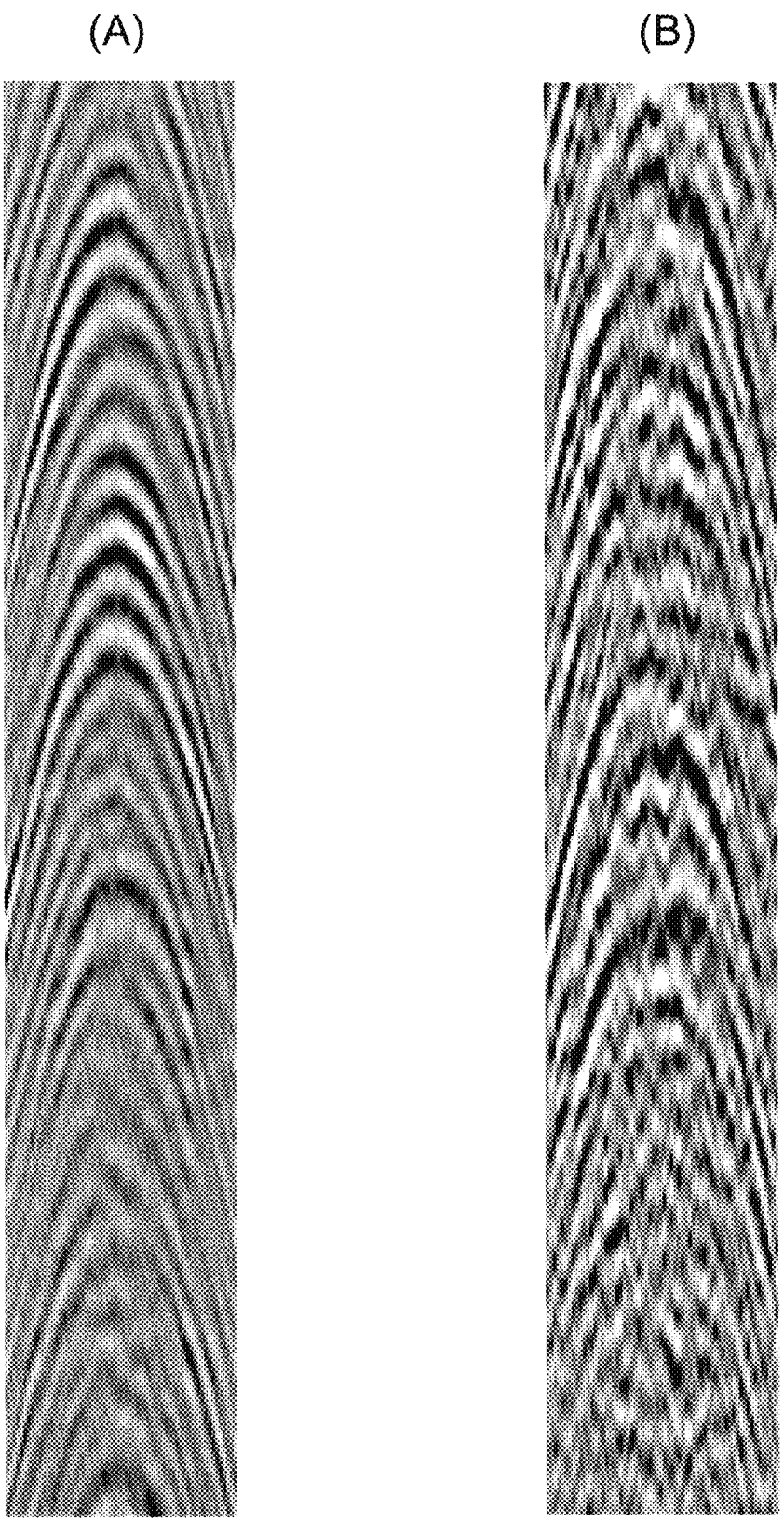
FIG. 11 depicts an image representing a received signal with a uniform wavefront in (A) portion, and depicts an image representing a received signal with a varied wavefront in (B) portion.

FIG. 11 depicts an example of a varied received signal.

In FIG. 11, the horizontal axis represents the position of an element, the vertical axis represents reception time, and gray scales each represent the amplitude of a received signal.

(A) portion of FIG. 11 depicts a received signal with a uniform wavefront. The wavefront is in a parabolic shape, which indicates that the received signal arrives at the center element first. Also, (B) portion of FIG. 11 depicts a received signal with a varied wavefront.

As such, in the present invention, a target is measured while including an influence of ambient scattering that occurs due to unevenness in sound velocity, attenuation, and scattering in formation of pseudo point reflection with transmission focus.

While various sonic or attenuation variation indexes based on a change in reception time, amplitude, or center frequency and various variation indexes based on a change in average sonic velocity or average attenuation due to the position of the point of interest have been described above, the present invention is not restricted to these examples above, and it goes without saying that other various variation indexes may be used within a range not deviating from the gist of the present invention. For example, after indexes of the respective points of interest in the region of interest based on the reception time, amplitude, or center frequency are all collected, skewness, kurtosis, or the like as their histogram shape feature amount may be taken as a variation index. Also, after the indexes for the respective points of interest are averaged, a standard deviation or a histogram shape feature amount of their distribution in the region of interest, or a texture feature amount from a cooccurrence matrix or the like, for example, uniformity, contrast, correlation, or entropy, may be used as a variation index.

Also, similarly, from a distribution of average sound velocities or average attenuations in the region of interest, a histogram feature amount, a texture feature mount, or the like can be taken as a variable index.

Furthermore, by not taking any of these feature amounts singly but from a plurality of feature amounts, a variation index may be found by using, for example, multiple regression.

By calculating an index representing a variation in sound velocity or attenuation (a variation index) in the manner described above, the tissue characteristic can be diagnosed with the use of this index.

For example, a large amount of data of specific lesions and their corresponding variations in sound velocity or attenuation are accumulated and, based on these data, a correspondence between values of the variation indexes and the states of tissue characteristics is statistically found, thereby setting a threshold of each variation index for diagnosing the tissue characteristic. Then, in actual diagnosis, a variation index is found by the method as described above, and is compared with the preset threshold, thereby diagnosing the tissue characteristic. With this, the tissue characteristic can be easily diagnosed.

As has been described above, in the present embodiment, not an absolute value of sound velocity or attenuation but a sonic variation or an attenuation variation is measured. Therefore, it is possible to grasp a microscopic change in sound velocity or attenuation structure due to a pathological change, the change being difficult to grasp with measurement of an absolute value of sound velocity or attenuation.

While the ultrasound diagnostic device and the ultrasound diagnostic method according to the present invention have been described in detail above, the present invention is not restricted to the examples described above, and it goes without saying that various improvements and modifications may be performed in a range not deviating from the gist of the present invention.

REFERENCE SIGNS LIST

10 . . . ultrasound diagnostic device, 100 . . . CPU, 104 . . . display unit, 106 . . . data analyzing and measuring unit, 200 . . . operation input unit, 300 . . . ultrasound probe, 302 . . . ultrasound transducer, 400 . . . transmitting and receiving unit, 500 . . . image signal generating unit, 502 . . . signal processing unit, 506 . . . image processing unit

The invention claimed is:

1. An ultrasound diagnostic device comprising:
an ultrasound probe including a plurality of ultrasound transducers configured to transmit ultrasound waves to an object and to receive ultrasound waves reflected from the object to output an ultrasound detection signal; and
a computer configured to perform transmission focus of the ultrasound waves on a single point of interest in the object;
wherein the computer is configured to perform transmission focus of the ultrasound waves on the single point of interest to transmit the ultrasound waves to the single point of interest to form a pseudo point reflection at the single point of interest, the pseudo point reflection including receiving the ultrasound waves reflected from a pseudo reflection source that is a focusing point of the transmission focus, and
wherein the computer is configured to measure a variation of a sound velocity in each of propagation paths of the ultrasound waves from each of the ultrasound transducers to the single point of interest, and propagation paths of the ultrasound waves from the single point of interest to each of the ultrasound transducers, based on a variation of received signals at each of the ultrasound transducers regarding the reflected ultrasound waves from the single point of interest, wherein the variation of the received signals is a variation from a reception time that is calculated on condition that the sound velocity in each of the propagation paths is constant.

2. The ultrasound diagnostic device according to claim 1, wherein the computer is configured to evaluate the variation of the sound velocity in the object based on a cross relation of a reception time or a phase of the received signals at each of the ultrasound transducers.

3. The ultrasound diagnostic device according to claim 1, wherein the computer obtains received signals at each of the ultrasound transducers from a first point which is positioned at a region shallower than the single point of interest with respect to a depth direction of the object, and evaluates a variation of acoustic characteristics in a region including the single point of interest and the first point in the object based on the received signals at each of the ultrasound transducers regarding the reflected ultrasound waves from the single point of interest and received signals at each of the ultrasound transducers regarding the reflected ultrasound waves from the first point.

4. The ultrasound diagnostic device according to claim 3, wherein the computer is configured to perform transmission focus of the ultrasound waves on the single point of interest and the first point when the received signals at each of the ultrasound transducers are obtained from the single point of interest and the first point.

5. The ultrasound diagnostic device according to claim 3, wherein the computer is configured to evaluate a change in the received signals due to a uniform component of the acoustic characteristics from a position of interest to each of the ultrasound transducers when the computer evaluates the variation of acoustic characteristics in the object based on a cross relation of the received signals at each of the ultrasound transducers.

6. The ultrasound diagnostic device according to claim 3, further comprising:
a display unit configured to display a result of an evaluation of the variation of the acoustic characteristics.

7. The ultrasound diagnostic device according to claim 6, wherein said computer further comprises:
an amplitude image generating unit configured to generate an amplitude image which represents an amplitude of the ultrasound detection signal with brightness of dots,
wherein the display unit displays a result of evaluation of the variation of the acoustic characteristics as superposed on the amplitude image, or displays the amplitude image and the result of evaluation of the variation of the acoustic characteristics which are arranged in a tiled manner.

8. The ultrasound diagnostic device according to claim 7, wherein the computer switches a display mode between a first display mode in which the amplitude image is displayed alone and a second display mode in which the result of evaluation of the variation of the acoustic characteristics is displayed, in accordance with an operation input from an operator accepted by the computer.

9. The ultrasound diagnostic device according to claim 6, wherein said computer is configured to generate an amplitude image which represents an amplitude of the ultrasound detection signal with brightness of dots,
wherein the display unit displays a result of evaluation of the variation of the acoustic characteristics by varying luminance in the amplitude image or coloring the amplitude image.

10. The ultrasound diagnostic device according to claim 9,
wherein the computer switches a display mode between a first display mode in which the amplitude image is displayed alone and a second display mode in which the result of evaluation of the variation of the acoustic characteristics is displayed, in accordance with an operation input from an operator accepted by the computer.

11. A method performed by an ultrasound diagnostic device comprising an ultrasound probe including a plurality of ultrasound transducers configured to transmit ultrasound waves to an object and to receive ultrasound waves reflected from the object to output an ultrasound detection signal, and a computer configured to perform transmission focus of the ultrasound waves on a single point of interest in the object, the method comprising:

performing transmission focus of the ultrasound waves on the single point of interest to transmit the ultrasound waves to the single point of interest to form a pseudo point reflection at the single point of interest, the pseudo point reflection including receiving the ultrasound waves reflected from a pseudo reflection source that is a focusing point of the transmission focus;

receiving ultrasound waves reflected from the single point of interest to output an ultrasound detection signal; and measuring a variation of a sound velocity in each of propagation paths of the ultrasound waves from each of the ultrasound transducers to the single point of interest, and propagation paths of the ultrasound waves from the single point of interest to each of the ultrasound transducers, based on a variation of received signals at each of the ultrasound transducers regarding the reflected ultrasound waves from the single point of interest, wherein the variation of the received signals is a variation from a reception time that is calculated on condition that the sound velocity in each of the propagation paths is constant.

12. An ultrasound diagnostic device comprising:

an ultrasound probe including a plurality of ultrasound transducers configured to transmit ultrasound waves to an object and to receive ultrasound waves reflected from the object, to output an ultrasound detection signal; and a computer configured to perform transmission focus of the ultrasound waves on a single point of interest in the object;

wherein the computer is configured to perform transmission focus of the ultrasound waves on the single point of interest to transmit the ultrasound waves to the single point of interest to form a pseudo point reflection at the single point of interest, the pseudo point reflection including receiving the ultrasound waves reflected from a pseudo reflection source that is a focusing point of the transmission focus, and wherein the computer is configured to measure a variation of an attenuation or scattering due to a mixture of media in each of entire propagation paths of the ultrasound waves from each of the ultrasound transducers to the single point of interest, and propagation paths of the ultrasound waves from the single point of interest to each of the ultrasound transducers, based on a variation of an amplitude or frequency of received signals at each of the ultrasound transducers regarding the reflected ultrasound waves from the single point of interest, wherein the variation of the amplitude or frequency is a variation from an amplitude or frequency that is calculated on condition that the attenuation or scattering in each of the propagation paths is constant.

13. The ultrasound diagnostic device according to claim 12, wherein the computer obtains received signals at each of the ultrasound transducers from a first point which is positioned at a region shallower than the single point of interest with respect to a depth direction of the object, and evaluates a variation of acoustic characteristics in a region including the single point of interest and the first point in the object based on the received signals at each of the ultrasound transducers regarding the reflected ultrasound waves from the single point of interest and received signals at each of the ultrasound transducers regarding the reflected ultrasound waves from the first point.

14. The ultrasound diagnostic device according to claim 13, wherein the computer is configured to perform transmission focus of the ultrasound waves on the single point of interest and the first point when the received signals at each of the ultrasound transducers are obtained from the single point of interest and the first point.

15. The ultrasound diagnostic device according to dairy 13, wherein the computer is configured to evaluate a change in the received signals due to a uniform component of the acoustic characteristics from a position of interest to each of the ultrasound transducers when the computer evaluates the variation of acoustic characteristics in the object based on a cross relation of the received signals at each of the ultrasound transducers.

16. The ultrasound diagnostic device according to claim 13, further comprising:

a display unit configured to display a result of an evaluation of the variation of the acoustic characteristics.

17. The ultrasound diagnostic device according to claim 16, wherein said computer is configured to generate an amplitude image which represents an amplitude of the ultrasound detection signal with brightness of dots, wherein the display unit displays a result of evaluation of the variation of the acoustic characteristics by varying luminance in the amplitude image or coloring the amplitude image.

18. The ultrasound diagnostic device according to claim 16, wherein said computer further comprises:

an amplitude image generating unit configured to generate an amplitude image which represents an amplitude of the ultrasound detection signal with brightness of dots, wherein the display unit displays a result of evaluation of the variation of the acoustic characteristics as superposed on the amplitude image, or displays the amplitude image and the result of evaluation of the variation of the acoustic characteristics which are arranged in a tiled manner.

19. The ultrasound diagnostic device according to claim 18, wherein the computer switches a display mode between a first display mode in which the amplitude image is displayed alone and a second display mode in which the result of evaluation of the variation of the acoustic characteristics is displayed, in accordance with an operation input from an operator accepted by the computer.

20. A method performed by an ultrasound diagnostic device comprising an ultrasound probe including a plurality of ultrasound transducers configured to transmit ultrasound waves to an object and to receive ultrasound waves reflected from the object to output an ultrasound detection signal, and a computer configured to perform transmission focus of the ultrasound waves on a single point of interest in the object, the method comprising:

performing transmission focus of the ultrasound waves on the single point of interest to transmit the ultrasound waves to the single point of interest to form a pseudo point reflection at the single point of interest, the pseudo point reflection including receiving the ultrasound waves reflected from a pseudo reflection source that is a focusing point of the transmission focus;
receiving ultrasound waves reflected from the single point of interest to output an ultrasound detection signal;
measuring a variation of an attenuation or scattering due to a mixture of media in each of entire propagation paths of the ultrasound waves from each of the ultrasound transducers to the single point of interest, and propagation paths of the ultrasound waves from the single point of interest to each of the ultrasound transducers, based on a variation of an amplitude or frequency of received signals at each of the ultrasound transducers regarding the reflected ultrasound waves from the single point of interest, wherein the variation of the amplitude or frequency is a variation from an amplitude or frequency that is calculated on condition that the attenuation or scattering in each of the propagation paths is constant.

* * * * *